(12) United States Patent
Shaw et al.

(10) Patent No.: US 11,609,214 B2
(45) Date of Patent: Mar. 21, 2023

(54) SYSTEMS AND METHODS FOR IMPROVING DETECTION ACCURACY IN ELECTRONIC TRACE DETECTORS

(71) Applicant: Rapiscan Systems, Inc., Torrance, CA (US)

(72) Inventors: Bradley Douglas Shaw, Plaistow, NH (US); William Rogers, Somerville, MA (US); Vladimir Romanov, Pelham, NH (US); Adam Justin Maines, Steamboat Springs, CO (US)

(73) Assignee: Rapiscan Systems, Inc., Torrance, CA (US)

( * ) Notice: Subject to any disclaimer, the term of this patent is extended or adjusted under 35 U.S.C. 154(b) by 790 days.

(21) Appl. No.: 16/527,966

(22) Filed: Jul. 31, 2019

(65) Prior Publication Data

US 2021/0033583 A1 Feb. 4, 2021

(51) Int. Cl.
 *G01N 33/00* (2006.01)
 *B01D 53/26* (2006.01)

(52) U.S. Cl.
 CPC ......... *G01N 33/0006* (2013.01); *B01D 53/26* (2013.01); *G01N 33/006* (2013.01); *G01N 33/0014* (2013.01); *G01N 33/0029* (2013.01)

(58) Field of Classification Search
 CPC ... G01N 33/0006; G01N 33/006; B01D 53/26
 See application file for complete search history.

(56) References Cited

U.S. PATENT DOCUMENTS

| | | | |
|---|---|---|---|
| 3,067,560 A | 12/1962 | Frederick |
| 3,705,480 A | 12/1972 | Wireman |
| 4,858,335 A | 8/1989 | Roth |
| 5,350,442 A | 9/1994 | Thelen |
| 5,491,337 A | 2/1996 | Jenkins |
| 5,554,846 A | 9/1996 | Regiec |
| 5,719,392 A | 2/1998 | Franzen |
| 5,970,804 A | 10/1999 | Robbat, Jr. |
| 6,211,516 B1 | 4/2001 | Syage |
| 6,225,623 B1 | 5/2001 | Turner |
| 6,326,615 B1 | 12/2001 | Syage |
| 6,329,653 B1 | 12/2001 | Syage |
| 6,534,765 B1 | 3/2003 | Robb |
| 6,630,664 B1 | 10/2003 | Syage |

(Continued)

FOREIGN PATENT DOCUMENTS

| | | |
|---|---|---|
| AT | 303589 T | 9/2005 |
| AT | 480769 T | 9/2010 |

(Continued)

OTHER PUBLICATIONS

International Search Report for PCT/US19/44410, dated Nov. 21, 2019.

(Continued)

*Primary Examiner* — Paul M. West
(74) *Attorney, Agent, or Firm* — Novel IP

(57) ABSTRACT

Embodiments of the present specification provide methods and systems for maintaining accuracy and precision of calibration for a detector. The methods and systems include reducing the humidity of an internal calibration assembly by directing flow path of dry air periodically through the internal calibration assembly.

24 Claims, 16 Drawing Sheets

(56) References Cited

U.S. PATENT DOCUMENTS

| | | |
|---|---|---|
| 6,642,513 B1 | 11/2003 | Jenkins |
| 6,690,005 B2 | 2/2004 | Jenkins |
| 6,708,572 B2 | 3/2004 | Jenkins |
| 6,737,642 B2 | 5/2004 | Syage |
| 6,765,198 B2 | 7/2004 | Jenkins |
| 6,815,670 B2 | 11/2004 | Jenkins |
| 6,831,273 B2 | 12/2004 | Jenkins |
| 6,840,122 B1 | 1/2005 | Jenkins |
| 7,014,683 B2 | 3/2006 | Vierling |
| 7,047,829 B2 | 5/2006 | Napoli |
| 7,109,476 B2 | 9/2006 | Hanold |
| 7,119,342 B2 | 10/2006 | Syage |
| 7,141,786 B2 | 11/2006 | McGann |
| 7,161,144 B2 | 1/2007 | Syage |
| 7,196,325 B2 | 3/2007 | Syage |
| 7,253,727 B2 | 8/2007 | Jenkins |
| 7,299,710 B2 | 11/2007 | Syage |
| 7,320,725 B2 | 1/2008 | Arno |
| 7,338,638 B2 | 3/2008 | McGann |
| 7,361,206 B1 | 4/2008 | Jahn |
| 7,401,498 B2 | 7/2008 | Syage |
| 7,448,248 B2 | 11/2008 | Carey |
| 7,456,393 B2 | 11/2008 | Napoli |
| 7,528,367 B2 | 5/2009 | Haigh |
| 7,541,577 B2 | 6/2009 | Davenport |
| 7,594,422 B2 | 9/2009 | Perry |
| 7,594,447 B2 | 9/2009 | Napoli |
| 7,663,099 B2 | 2/2010 | Reda |
| 7,721,588 B2 | 5/2010 | Perry |
| 7,799,567 B1 | 9/2010 | Call |
| 7,856,898 B2 | 12/2010 | Carey |
| 7,880,137 B2 | 2/2011 | McGann |
| 8,161,830 B2 | 4/2012 | Boudries |
| 8,186,234 B2 | 5/2012 | Syage |
| 8,288,735 B2 | 10/2012 | Syage |
| 8,402,842 B2 | 3/2013 | Syage |
| 8,434,375 B1 | 5/2013 | Syage |
| 8,614,582 B2 | 12/2013 | Syage |
| 8,686,355 B2 | 4/2014 | Patterson |
| 8,723,111 B2 | 5/2014 | Syage |
| 8,857,278 B2 | 10/2014 | Syage |
| 8,866,073 B2 | 10/2014 | Goedecke |
| 8,952,327 B2 | 2/2015 | Patterson |
| 9,147,565 B1 | 9/2015 | Goedecke |
| 9,354,153 B2 | 5/2016 | Syage |
| 9,482,655 B2 | 11/2016 | Vilkov |
| 9,528,969 B2 | 12/2016 | Shaw |
| 9,558,924 B2 | 1/2017 | Syage |
| 9,683,981 B1 | 6/2017 | Vilkov |
| 9,689,857 B1 | 6/2017 | Vilkov |
| 9,726,655 B2 | 8/2017 | Syage |
| 9,766,218 B2 | 9/2017 | Lai |
| 9,789,434 B1 | 10/2017 | Lai |
| 2003/0164091 A1 | 9/2003 | Hill |
| 2004/0089799 A1 | 5/2004 | Kawato |
| 2004/0262512 A1 | 12/2004 | Tobita |
| 2005/0061964 A1 | 3/2005 | Nagano |
| 2007/0028670 A1 | 2/2007 | Bonne |
| 2008/0098794 A1* | 5/2008 | Perry .............. G01N 1/2214 73/1.06 |
| 2008/0191129 A1 | 8/2008 | Makarov |
| 2009/0152458 A1 | 6/2009 | Vilkov |
| 2009/0159790 A1 | 6/2009 | Kostiainen |
| 2011/0272571 A1 | 11/2011 | Kenttaemaa |
| 2012/0037797 A1 | 2/2012 | Li |
| 2012/0112061 A1 | 5/2012 | Morokuma |
| 2014/0264002 A1 | 9/2014 | Goedecke |
| 2015/0285780 A1 | 10/2015 | Kelley |
| 2016/0282304 A1 | 9/2016 | Vilkov |
| 2017/0103880 A1 | 4/2017 | Syage |
| 2017/0213715 A1 | 7/2017 | Davila |
| 2017/0261483 A1 | 9/2017 | Vilkov |
| 2017/0261484 A1 | 9/2017 | Vilkov |
| 2017/0284977 A1 | 10/2017 | Rogers |
| 2017/0309463 A1 | 10/2017 | Vilkov |
| 2018/0158665 A1 | 6/2018 | Eiceman |
| 2018/0164189 A1 | 6/2018 | Bilodeau |
| 2018/0172635 A1 | 6/2018 | Lai |
| 2018/0172650 A1 | 6/2018 | Platow |
| 2018/0182603 A1 | 6/2018 | Schmidt |
| 2018/0182604 A1 | 6/2018 | Lai |
| 2018/0283993 A1 | 10/2018 | Shaw |
| 2018/0284081 A1 | 10/2018 | Shaw |
| 2018/0356320 A1 | 12/2018 | Romanov |
| 2019/0011421 A1 | 1/2019 | Rogers |
| 2019/0046974 A1 | 2/2019 | Meketa |
| 2019/0204274 A1 | 7/2019 | Eiceman |
| 2019/0228959 A1 | 7/2019 | Verkerk |
| 2020/0072791 A1* | 3/2020 | Boudries .............. G01N 27/626 |

FOREIGN PATENT DOCUMENTS

| | | |
|---|---|---|
| CA | 2153371 C | 3/1999 |
| CA | 2436256 C | 6/2007 |
| CA | 2382823 C | 11/2007 |
| CA | 2362449 C | 10/2008 |
| CA | 2411532 C | 4/2010 |
| CA | 2285153 C | 5/2010 |
| CA | 2479875 C | 2/2011 |
| CA | 2538709 C | 2/2013 |
| CA | 2790430 A1 | 3/2013 |
| CA | 2807894 A1 | 9/2013 |
| CA | 2620405 C | 7/2014 |
| CA | 2548177 C | 9/2014 |
| CA | 2844222 A1 | 9/2014 |
| CA | 2845959 A1 | 9/2014 |
| CA | 2688352 C | 6/2015 |
| CA | 2644937 C | 11/2015 |
| CA | 2904479 A1 | 3/2016 |
| CA | 2910780 A1 | 4/2016 |
| CA | 2913931 A1 | 6/2016 |
| CA | 2915785 A1 | 6/2016 |
| CA | 2924580 A1 | 9/2016 |
| CA | 2647651 C | 11/2016 |
| CA | 2738053 C | 5/2017 |
| CA | 2959791 A1 | 9/2017 |
| CA | 2959796 A1 | 9/2017 |
| CA | 2962154 A1 | 9/2017 |
| CA | 2964147 A1 | 10/2017 |
| CN | 101093211 A | 12/2007 |
| CN | 101120247 A | 2/2008 |
| CN | 100445767 C | 12/2008 |
| CN | 101600960 A | 12/2009 |
| CN | 103308590 A | 9/2013 |
| CN | 103367092 A | 10/2013 |
| CN | 103650102 A | 3/2014 |
| CN | 105738461 A | 7/2016 |
| CN | 107037114 A | 8/2017 |
| CN | 107167334 A | 9/2017 |
| CN | 107167335 A | 9/2017 |
| CN | 107271254 A | 10/2017 |
| DE | 69528418 T2 | 1/2003 |
| DE | 69926965 T2 | 6/2006 |
| EP | 1048540 A1 | 11/2000 |
| EP | 1517129 A2 | 3/2005 |
| EP | 2368102 A2 | 9/2011 |
| EP | 2587259 A1 | 5/2013 |
| EP | 2637013 A2 | 9/2013 |
| EP | 2778650 A2 | 9/2014 |
| EP | 2778669 A1 | 9/2014 |
| EP | 2884254 A1 | 6/2015 |
| EP | 3015858 A1 | 5/2016 |
| EP | 3032570 A2 | 6/2016 |
| EP | 3040717 A1 | 7/2016 |
| EP | 1938078 B1 | 3/2017 |
| EP | 1297554 B1 | 4/2017 |
| EP | 3182111 A1 | 6/2017 |
| ES | 2183855 | 4/2003 |
| FR | 692712 A | 11/1930 |
| GB | 992782 A | 5/1965 |
| GB | 2075578 A | 11/1981 |
| GB | 2496286 A | 5/2013 |
| GB | 2536076 A | 9/2016 |
| JP | 3045655 B2 | 5/2000 |

(56) References Cited

FOREIGN PATENT DOCUMENTS

| JP | 2006064325 | 3/2006 |
| WO | 0209847 A2 | 2/2002 |
| WO | 2008060666 A2 | 5/2008 |
| WO | 2009023361 A2 | 2/2009 |

OTHER PUBLICATIONS

Cody et al., "Versatile New Ion Source for the Analysis of Materials in Open Air under Ambient Conditions", Anal. Chem., 2005, vol. 77, pp. 2297-2302.

* cited by examiner (ALTERNATE EMBODIMENT)

| % relative Humidity | Dopant flow (lpm) | Pos long |
|---|---|---|
| 0.36% | 0.195 | 2 peaks |
| 5.70% | 0.300 | 2 peaks |
| 6.40% | 0.430 | 2 peaks |
| 7.27% | 0.450 | 2 peaks |
| 7.72% | 0.460 | 2 peaks |
| 8.02% | 0.500 | 1 peak |
| 8.27% | 0.560 | 1 peak |
| 10.90% | 0.980 | 1 peak |

FIG. 8A

SYSTEMS AND METHODS FOR IMPROVING DETECTION ACCURACY IN ELECTRONIC TRACE DETECTORS

CROSS REFERENCE

The present specification relates to U.S. patent application Ser. No. 15/388,589 entitled "Systems and Methods for Calibration, Verification, and Sensitivity Checks for Detectors", filed on Dec. 22, 2016, and is hereby incorporated by reference in its entirety.

The present specification relates to U.S. patent application Ser. No. 15/379,834 entitled "Methods and Devices for Moisture-Based Calibration", filed on Dec. 15, 2016, and is hereby incorporated by reference in its entirety.

FIELD

The present specification relates to improving the precision and accuracy of Electronic Trace Detectors (ETD) operation. More particularly, the present specification relates to reducing the variability of calibration in the ETD by limiting the amount of moisture in an internal calibration assembly.

BACKGROUND

Electronic Trace Detectors (ETDs) require calibration to ensure precise and accurate operation. To facilitate calibration, an automatic procedure is typically run periodically throughout the shift. The procedure includes using a canister of a calibrant chemical sealed between solenoid valves and plastic tubing. At an appropriate time, valves are activated and the flow path is diverted past the canister, pulling the calibrant chemical into the ETD. This subsystem is referred to as the internal calibrant assembly (ICA).

Preferably, the humidity level in the ICA is uniform with the rest of the instrument. A desired humidity level, which may also be referred to as the target Relative Humidity (RH), in the ICA is very low, e.g. less than 1% RH. However, over time and with fluctuating weather conditions, the humidity slowly increases in the ICA. This can be caused by tiny leaks and permeation though the plastic tubing walls. This phenomenon is exacerbated by longer tubing length with dead volume. Additional humidity may cause further issues with the operation and calibration of the ETD.

FIG. 1 is a plot showing an example of how each substance peak can shift by different amounts (in arbitrary time units) at a given humidity level. At a low humidity level, the peak shifts are largely uniform. As shown in FIG. 1, with increasing humidity, the time of flight peaks can be shifted which results in improper calibration of the ETD. When this happens, the system is not useable and requires maintenance. In addition, the degree of the shifting is not uniform for all compounds. Having uniform peak shifts improves analytical processes because humidity-based adjustments are not required, and the analyses can just focus on drift time. One of ordinary skill in the art would appreciate that measuring a single variable is easier than measuring two variables and adjusting for variations in both variables.

ETDs are known to use an internal calibrant with moisture. However such calibration has been observed to be inaccurate and not precise. Scrubbers (molecular sieve cartridges, Nafion tubes, charcoal, desiccant, others) are also specifically known to be used for an ICA. However, without regenerative capabilities, scrubbers need to be replaced constantly, which is not desirable. Another option is to have different calibration libraries that are used at pre-determined humidity levels, which requires an in-line moisture sensor. This approach is known to be used in Differential Mobility Spectrometry (DMS) systems. These known methods accept variable humidity levels and do not remove humidity from the system.

U.S. Pat. No. 7,964,017, assigned to General Dynamics Armament and Technical Products, Inc., discloses "[a] gas flow system and method for controlling the moisture in a gas flow. The system may include a gas source from which gas flows, a processing chamber to which the gas flows, and a gas flow line through which the gas flows from the gas source to the processing chamber. The gas flow line may include a moisture control line section. The moisture control line section includes a pass-through line through which the gas may pass, so as to be exposed to a dryer. The exposure to a dryer may be controlled by a suitable valve. A scrubber is disposed in the gas flow line, the scrubber removing contaminates from the gas in the gas flow. The system may include a moisture sensor disposed in the gas flow, the moisture sensor sensing at least one parameter of the gas and outputting a signal representing the at least one parameter to a moisture sensor controller, such that the moisture sensor controller determines the moisture in the gas. The moisture sensor controller controls the flow of the gas so as to control the moisture in the gas by adjusting the valve."

In addition, U.S. Pat. No. 6,815,670, assigned to the Applicant of the present specification, discloses "[a] detector apparatus comprising: a detector for detecting trace amounts of particles of interest carried on a stream of air; two dryers in communication with the stream of air; at least one valve in communication with the dryers for selectively placing a first of the dryers in communication with the detector; and at least one heater for selectively recharging a second of the dryers while the first dryer is in communication with the detector."

U.S. Patent Application No. 20180182603, assigned to the Applicant of the present specification, and incorporated herein by reference, is directed to "methods and systems for calibration, calibration verification, and sensitivity checks for a detector." The methods and systems include calibrating a detector by releasing at least one calibrant from at least one calibrant chamber in flow communication with the detector. The systems and methods further include verifying the calibration by releasing at least one verification substance from at least one verification chamber in flow communication with the detector. The systems and methods further include checking a sensitivity of the detector by releasing at least one sensitivity substance from at least one sensitivity chamber in flow communication with the detector."

In order to reduce humidity levels, ETDs can be designed with metal tubing, seals, and high vacuum solenoid valves in the ICA. While such a design would slow the permeation of moisture into the ICA, it would increase the cost of the ETD, and is therefore not desirable.

During a typical day of operation at an airport, which may start using ETDs early in the morning, peaking during the day, and purged at night, it is desirable that the relative humidity in the ICA is preferably maintained at a constant level, and in some cases does not increase by more than 2%. At the same time, it is also desirable to enable optimal operational time of the ETDs with minimal downtime in order to reduce the relative humidity levels in the ICA. It is further desirable to reduce the need to introduce a calibrant too often into the ICA, as introducing the calibrant too often decreases system throughput. It is also desirable to reduce redundant systems, such as multiple sets of dry air sources, which will increase the size and cost of the ETDs. Thus, there is a need for methods and systems for reducing the relative humidity in the ICA. In addition, there is a need for maintaining the humidity level consistent at various ambient conditions which results in reproducible calibration of the system. There is also a need for diagnostic tool to determine when the humidity inside ICA is too high.

SUMMARY

The following embodiments and aspects thereof are described and illustrated in conjunction with systems, tools and methods, which are meant to be exemplary and illustrative, not limiting in scope.

The present specification discloses a method for reducing humidity within an internal calibration chamber of a trace detection system, wherein the trace detection system comprises a first pump coupled with a dryer, a desorber in flow communication with the first pump, a detector in flow communication with the desorber, and an internal calibration assembly defined by a housing and having a first valve, a second valve, and a calibrant source positioned within the housing, wherein when the first valve is in a first state it directs flow directly to at least one of the desorber or the second valve and bypasses the calibrant source and wherein, when the first valve is in a second state, it directs flow through the calibrant source and then to the second valve, the method comprising: in a first mode of operation, operating the first pump to direct air through the dryer in order to form dry air; and operating the first valve to place the first valve in the first state, wherein the first valve is configured to receive the dry air and direct the dry air to the desorber without being in flow communication with the calibrant source; and in a second mode of operation, operating the first pump to direct air through the dryer in order to form dry air; and operating the first valve to place the first valve in the second state, wherein the first valve is configured to receive the dry air and direct the dry air through the second valve and the calibrant source to the desorber.

Optionally, the method further comprises, in the first mode of operation, operating the first valve to direct dry air to the desorber without being in flow communication with the second valve.

Optionally, in the second mode of operation, the dry air has a relative humidity of less than 1%.

Optionally, the calibrant source comprises a canister of calibration chemical. Optionally, the calibrant is at least one of dibenzylamine, diethylphenylmalonate, diisopropylphenol, 2,4-dimethylpyridine, dioctylphthalate, dinitrotoluene, dipropylene glycol monomethylether, 2,6-di-t-butylpyridine, ethyl salicylate, hexachloroethane, hexaphenylbenzene, 4-methyl-2,6-di-tert-butyl phenol, methyl salicylate, nicotinamide, 4-nitrobenzonitrile, 5-nitrovanillin, pentachloroethane, trihexylamine, or combinations thereof.

Optionally, the internal calibrant assembly is not in flow communication with the trace detection system except through the second valve.

Optionally, each of the first valve and second valve comprise at least two ports.

Optionally, a flow rate of the air in each of the first mode of operation and second mode of operation is in a range from about 5 mL per minute to about 5000 mL per minute.

Optionally, in a given 24 hour period, the second mode of operation is activated at a plurality of intervals wherein each of the plurality of intervals ranges from a minimum of 30 minutes to a maximum of 24 hours.

Optionally, the second mode of operation is performed at least once between 10 p.m. and 6 a.m.

Optionally, a relative humidity within the internal calibration assembly does not exceed 3%.

Optionally, a relative humidity within the internal calibration assembly does not exceed 6%.

The present specification also discloses a trace detection system comprising: a first housing; an internal calibration assembly defined by a second housing and having a first valve, a second valve, and calibrant source positioned within the second housing; a first pump positioned in the first housing and outside the second housing; a desorber in flow communication with the first pump and positioned in the first housing and outside the second housing; a detector in flow communication with the desorber and positioned in the first housing and outside the second housing; and a controller configured to operate the trace detection system in a first mode and in a second mode, wherein, in the first mode of operation, the controller is configured to operate the first pump to direct air through the dryer to form dry air and direct the dry air to the desorber through the first valve without being in flow communication with the calibrant source; and wherein, in the second mode of operation, the controller is configured to operate the first pump to direct air through the dryer to form dry air, and direct the dry air through the second valve and the calibrant source to the desorber.

Optionally, in the first mode of operation, the controller is configured to operate the first valve to direct the dry air directly to the desorber without being in flow communication with the second valve.

Optionally, in the second mode of operation, the dry air has a relative humidity of less than 1%.

Optionally, the calibrant source comprises a canister of calibration chemical.

Optionally, the internal calibrant assembly is only in flow communication with other components of the trace detection system through the second valve.

Optionally, each of the first valve and the second valve comprise at least two ports.

Optionally, a flow rate of the dry air in each of the first mode of operation and the second mode of operation is in a range from about 5 mL per minute to about 5000 mL per minute.

Optionally, the calibrant is at least one of dibenzylamine, diethylphenylmalonate, diisopropylphenol, 2,4-dimethylpyridine, dioctylphthalate, dinitrotoluene, dipropylene glycol monomethylether, 2,6-di-t-butylpyridine, ethyl salicylate, hexachloroethane, hexaphenylbenzene, 4-methyl-2,6-di-tert-butyl phenol, methyl salicylate, nicotinamide, 4-nitrobenzonitrile, 5-nitrovanillin, pentachloroethane, trihexylamine, or combinations thereof.

Optionally, the controller is configured to operate the second mode of operation at regular intervals in a 24 hour period, wherein a time period of the regular intervals varies from a minimum of 30 minutes to a maximum of 24 hours.

Optionally, the controller is configured to operate the second mode of operation at least once during a nighttime cleaning process of the trace detection system.

Optionally, a relative humidity within the internal calibration assembly does not exceed 3%.

Optionally, a relative humidity within the internal calibration assembly does not exceed 6%.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 8A illustrates a table showing the peaks formed by a dopant in in a positive polarity region at different humidity levels;

DETAILED DESCRIPTION

Figure 1:
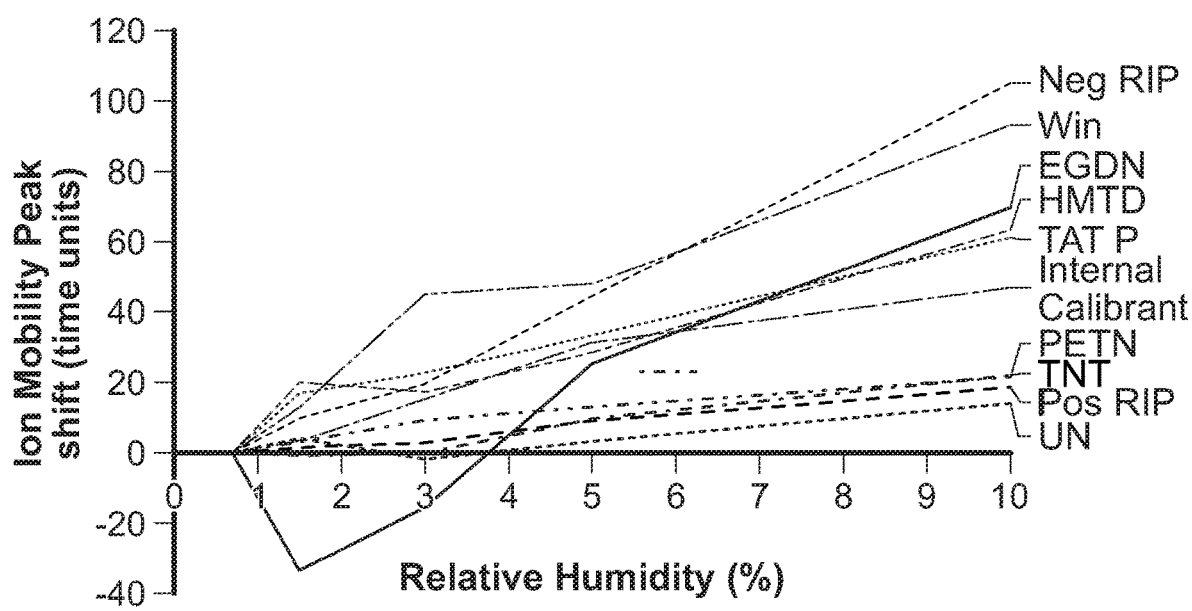
FIG. 1 is an exemplary plot showing how each substance peak can shift by different amounts of time relative to specific humidity levels.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present specification.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Definitions

Calibration: Calibration of ETDs is required to ensure continued precision and accuracy of their operation. During calibration, a known type of calibration substance is introduced either internally or externally into a detection system with the goal of associating a certain peak location (drift time in calibrated units) in the mobility spectrum/plasmagram with an absolute drift time.

Nightly clean: Refers to a protocol that is followed typically by operators of ETDs to perform a cleaning operation, including calibration, of the ETD at night or when the ETD is not expected to be in operation. For example, at most airports, the typical shift timings are from 5 AM to 12 AM, therefore the ETDs at these locations may undergo cleaning operation as a part of a scheduled maintenance activity between 12 AM and 5 AM. The nightly clean comprises using a thermal protocol to raise temperatures of various sub-systems to a "burn temperature" in order to purge contaminants, followed immediately by cooling to a temperature at which the ETD may operate. In embodiments, the nightly clean is a feature where the system elevates temperatures and opens valves in a way to clean the system so it is ready for the next day's operation.

Internal calibration chamber purge: Clean, dry air is drawn in to flush the internal calibration chamber that is included within an internal calibration assembly. Purging the internal calibration chamber ensures that it is devoid of any contaminants and/or environmental substances, such as humidity, that could affect the calibration process. In embodiments, the internal calibration chamber is purged as part of a nightly clean protocol and at regular intervals throughout the day. In embodiments, it involves a software feature that lowers humidity levels in the internal calibration pneumatics by opening additional valves as part of the nightly clean feature.

Internal calibration chamber purge regular interval: The frequency with which the ETD 100 performs the internal calibration chamber purge during the time when the ETD is expected to be in operation. In embodiments, a typical operator shift is from 5 AM to 12 AM (1,140 minutes) and this procedure takes 1 minute to complete. Therefore, if the regular interval were set to 30 minutes, the ETD would attempt 38 calibration purges in a regular shift which constitutes 3.3% of the time when the ETD is expected to be in operation.

Relative Humidity (RH): The term relative humidity (RH) is defined as the ratio of the amount of water vapor actually present in the air to the greatest amount possible at the same temperature. For example, when referring to the RH within an internal calibration chamber of an ETD or to the RH level of internal calibration pneumatics measured before entering curtain port, it would be preferable for the actual amount of water vapor in the air relative to the maximum possible water vapor in the air to be less than 1% in order to achieve accuracy in the calibration process.

Target humidity: Refers to the desired RH level within the internal calibration chamber of an ETD, which is desired and aimed to be achieved by the embodiments of the present specification, after a full purge.

DESCRIPTION

The calibration of an ETD is required to ensure continued precision and accuracy of its operation. Embodiments of the present specification provide methods and systems to reduce variability of calibration by reducing humidity in internal calibration systems used in ETDs. In the calibration process, a known type of calibration substance is introduced either internally or externally into the detection system of an ETD system, with the goal of associating a certain peak location (drift time in calibrated units) in the mobility spectrum or plasmagram with an absolute drift time. The analysis focuses on the drift time dimension (mobility axis), rather than on the intensity (peak height) dimension. In embodiments, an internal calibration chamber within an internal calibration assembly (ICA) of the ETD is purged as part of a nightly cleaning process and at regular intervals throughout the day. The ICA is opened to air flow to reduce moisture in the assembly. Embodiments of the present specification provide an automatic procedure that may be implemented periodically for ease of use.

In some cases, the nightly clean is performed during a time outside the shift time of operation of an ETD. In an example, ETDs at airports are operable during airport shift time which is typically between 5 AM and 12 AM. In this example, the nightly clean may be performed between 12 AM and 5 AM. The nightly clean may last for any period of time and typically ranges from 25 minutes and 5 hours. During the cleaning process, a temperature may be raised to a "burn temperature" and then immediately start cooling back down to an operating temperature, in order to remove contaminants from the system. In embodiments, at least 25 minutes are used to heat and cool the system. Since the system is heated to a burn temperature, the process is also termed as the nightly burn protocol. A nightly purge of the internal calibration chamber may be performed upon completion of the nightly burn protocol. In some embodiments, a nightly purge of the internal calibration chamber of approximately 20 minutes is adequate to maintain proper humidity levels during normal operation and 60 minutes is sufficient from a cold start. In some other embodiments, for a nightly burn protocol of approximately 1 hour, the first 20 minutes of this time is used to purge the internal calibration chamber of humidity. This may be done to minimize the purge time to consume the least amount of chemical calibrant, but still reduce the humidity to normal levels while also minimizing the time when the ETD is inoperable.

In embodiments, the internal calibration chamber of the ETD may also be purged at regular intervals throughout the day. In some cases, the interval may be repeated from every 30 minutes to every 8 hours. In an exemplary embodiment, where one operator shift is 1140 mins, if an ETD has a 30 minutes interval, and one calibration takes 1 minute to complete, then 38 calibrations occur in one shift, and 38/1140=3.3%. Hence, a 30 minute interval is equivalent to about 3.3% of the duration of an operation shift of the ETD as stated in the above example. of an airport. Whereas, in an 8 hour interval only 2 calibrations would occur and 2/1140=0.18%. Hence, an 8 hours interval is equivalent to about 0.18% of the duration of an operation shift of an ETD. If the interval was 8 hours then only 2 calibrations would occur and 2/1140=0.18%

Figure 2:
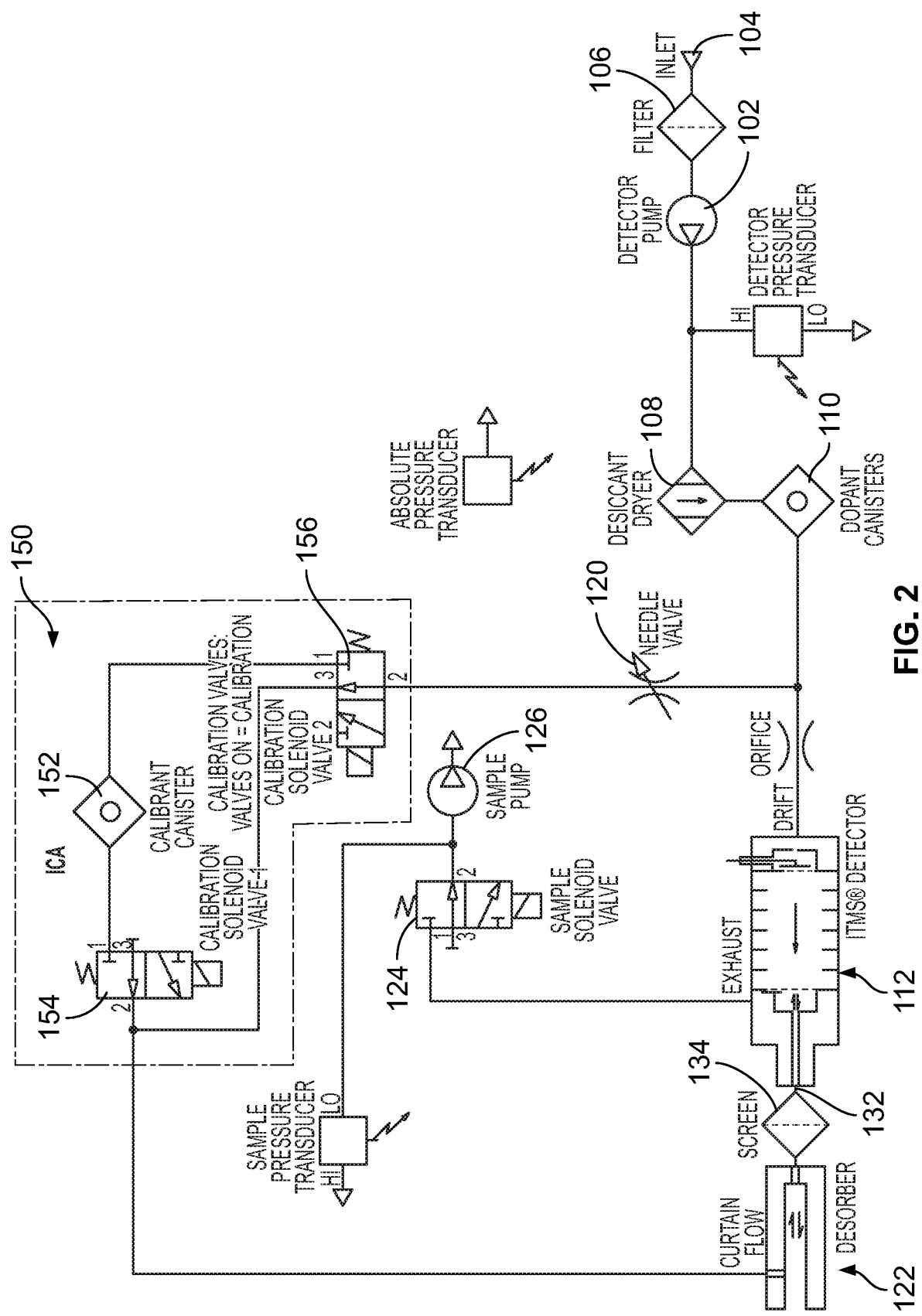
FIG. 2 shows a simplified pneumatic schematic of an ETD, in accordance with some embodiments of the present specification.

FIG. 2 depicts a simplified pneumatic schematic of an ETD 100, in accordance with some embodiments of the present specification. During sampling, an ionization source is used to ionize one or more substances (e.g., a sample, calibrant, verification substance, and/or sensitivity substance) within a detector 112. The ionization source may be any ionization system that enables operation of the methods and systems as described herein, including, without limitation, at least one of: a radioactive ionization source, an electrospray ionization source (ESI), an atmospheric pressure chemical ionization (APCI) source, a corona discharge ionization source, a partial discharge ionization source, an atmospheric pressure photoionization (APPI) source, an atmospheric pressure glow discharge (APGD) source, a direct analysis in real-time (DART) source, an atmospheric pressure dielectric barrier discharge (APDBD) source, and an electron ionizer (EI). In some embodiments of the present disclosure, the ionization source comprises at least one of an APCI source, an APPI source, an ESI source or a DART source. Some embodiments of the present disclosure are configured to operate at sub-atmospheric pressures. Such embodiments include an ionization source that is, without limitation, a chemical ionization (CI) source, a photoionization (PI) source, a glow discharge (GD) source, a dielectric barrier discharge (DBD) source and combinations thereof.

In some embodiments, detector 112 of the present disclosure (also referred to herein as an "analysis device") includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a mass spectrometer (MS), a gas chromatograph (GC), and combinations thereof.

Detector 112 is configured to detect and identify constituents in a sample input thereto. For example, in some embodiments, detector 112 is configured to detect one or more substances of interest in a sample gas, such as one or more volatile or non-volatile substances of interest. Detector 112 includes a detector inlet 132 through which substances enter detector 112.

A sample pump 126 is in flow communication with detector 112 via a sample valve 124. In the illustrated embodiment, valve 124 includes a three-way valve, such that, based on a position of valve 124, gas does or does not flow through valve 124. Upon activation, sample pump 126 creates a vacuum which pulls gas from detector 112 though valve 124.

In embodiments, system 100 further includes a computing device (not shown). In some embodiments, the computing device may be located remote from system 100. In some other embodiments, the computing device is integral to system 100. In some embodiments, the computing device includes a memory device and a processor operatively coupled to the memory device for executing instructions. In some embodiments, executable instructions are stored in the memory device. Computing device is configurable to perform one or more operations described herein by the programming processor. For example, in some embodiments, the processor is programmed by encoding an operation as one or more executable instructions and providing the executable instructions in the memory device. In the exemplary embodiment, the memory device is one or more devices that enable storage and retrieval of information such as executable instructions and/or other data. The memory device includes one or more computer readable media in some embodiments.

The memory device is configured to store a pre-programmed library of mobility spectra, each mobility spectrum associated with one substance of a plurality of substances. Memory device may further store associated drift times, alarm limits, detection history, calibration profiles and history (e.g., verification history) for detector 112 in system 100, and/or any other type of data in some embodiments. In the exemplary embodiment, the computing device, including the memory device, includes, without limitation, sufficient computer-readable/executable instructions, sufficient data and data structures, algorithms, and commands to facilitate detection of substance(s) introduced into detector 112 (e.g., a sample, the calibrant, the verification substance, and/or the sensitivity substance).

In the exemplary embodiment, system 100 further includes an operator presentation and/or control interface coupled to the computing device. The interface presents data, such as mobility spectra, calibration procedures, verification outcomes, and/or sensitivity check outcomes. In some embodiments, the interface includes one or more display devices. In some embodiments, the interface presents an audible and/or graphical notification upon detection of a substance of interest. Also, in some embodiments, the interface facilitates control of the computing device and manual data input into the computing device. Furthermore, in some embodiments, the computing device is coupled in communication with one or more other devices, such as another computing device, locally or remotely. As such, in some embodiments, system 100 is networked with other systems and devices such that data transmitted across portions of system 100 is accessed by any device capable of accessing the computing device including, without limitation, desktop computers, laptop computers, and personal digital assistants (PDAs) (neither shown).

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Figure 3:
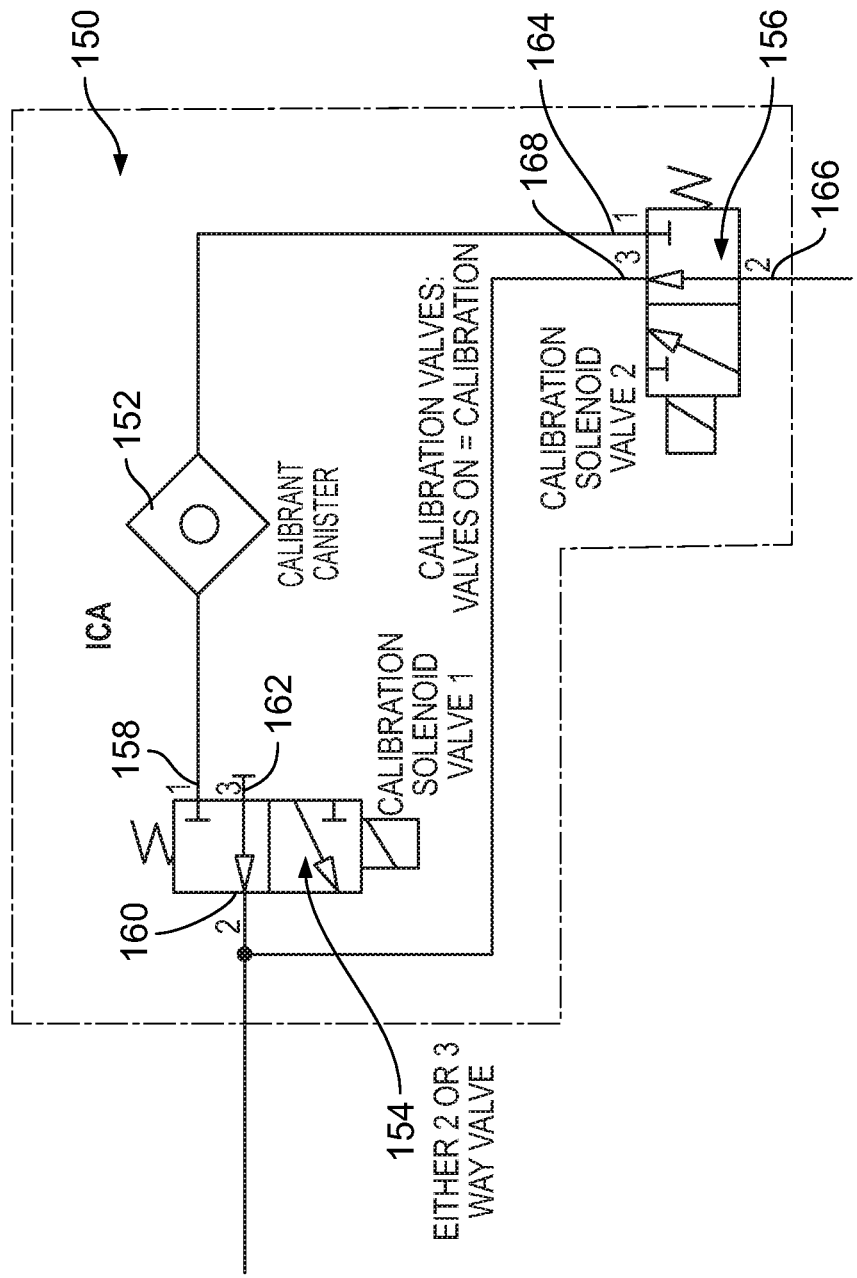
FIG. 3 is a zoomed-in view of an ICA chamber of the pneumatic schematic shown in FIG. 2.
Figure 4A:
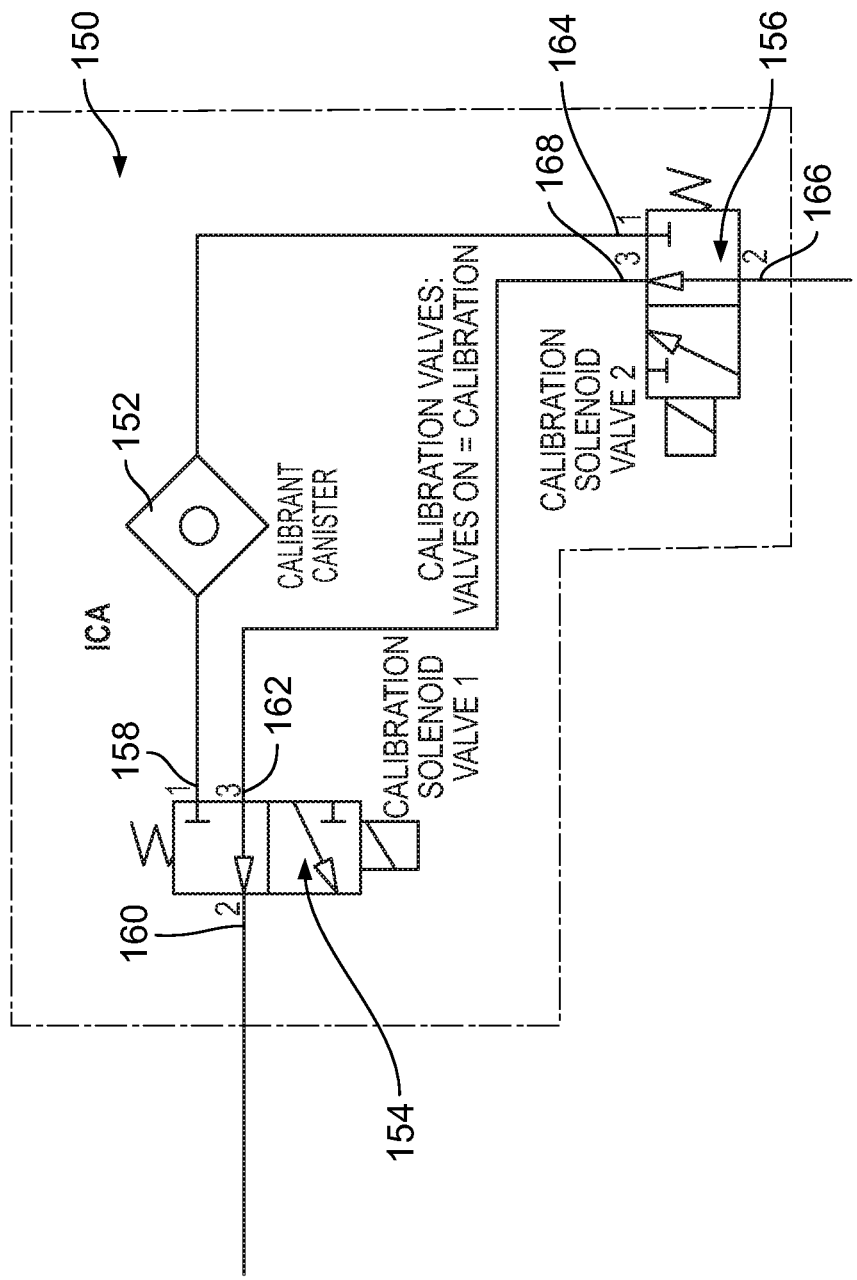
FIG. 4A shows an alternate configuration of the 'valve 1' for the ICA chamber shown in FIG. 3.

FIG. 2 further illustrates a component in the form of an internal calibrant assembly (ICA) located within a chamber 150 comprising a calibrant chemical in a sealed canister (seal) 152 between two valves—a first calibrant valve 154 and a second calibrant valve 156. Chamber 150 is preferably physically isolated from, physically distinct from, or otherwise isolated, except for the designated flow paths, from the rest of the housing or apparatus. FIG. 3 is an expanded view of ICA/chamber 150 of the schematic representation of ETD system 100 shown in FIG. 2. FIG. 4A shows an alternate embodiment of the valve 1 shown in FIG. 3. Referring to FIGS. 2, 3 and 4A, in some embodiments, valves 154 and 156 are solenoid valves. First valve 154 of chamber 150 is in flow communication with detector 112 through screen 134 and desorber 122. Second valve 156 of ICA chamber 150 is in flow communication with inlet 104 through filter 106, detector pump 102, dryer 108 and dopants 110.

When system 100 is operating to calibrate detector 112, valve 120 is positioned such that gas from detector pump 102 flows through valve 120 and through calibrant chamber 150. The gas includes at least one of ambient air, purified air, dried air, purified nitrogen, and combinations thereof. In an exemplary embodiment, the gas has a flow rate of from about 5 mL/min to about 5000 mL/min, from about 5 mL/min to about 1000 mL/min, from about 10 mL/min to about 100 mL/min, or from about 25 mL/min to about 50 mL/min. The gas flows through calibrant chamber 150 to "pick up" the calibrant therein and actively deliver the calibrant to detector 112 through desorber 122. The combination of gas and the calibrant carried therein is referred to herein as "calibrant gas". Calibrant chamber 150 is in flow communication with detector 112 via first valve 154. In the illustrated embodiment, valve 154 includes a two or three-way valve, such that, based on a position of valve 154, calibrant gas will flow through valve 154 to detector 112 or will not flow through valve 154. To calibrate detector 112, valve 154 is positioned such that calibrant gas flows through valve 154, through desorber 122, and to detector 112 for detection of the calibrant. Additionally or alternatively, system 100 channels the calibrant gas directly to detector 112, bypassing desorber 122.

In exemplary embodiments, the calibrant includes at least one of Dibenzylamine, Diethylphenylmalonate, Diisopropylphenol, 2,4-Dimethylpyridine, Dioctylphthalate, Dinitrotoluene, Dipropylene glycol monomethylether, 2,6-Di-t-butylpyridine, Ethyl salicylate, Hexachloroethane, Hexaphenylbenzene, 4-Methyl-2,6-di-tert-butyl phenol, Methyl salicylate, Nicotinamide, 4-Nitrobenzonitrile, 5-Nitrovanillin, Pentachloroethane, Trihexylamine, and combinations thereof. Whatever particular substance the calibrant is, the calibrant is known to detector 112 (e.g., to an operator thereof) prior to calibration of detector 112 using the calibrant. Detector 112 compares a detected signal of the calibrant to a library of expected signals representative of different substances, including the calibrant. Detector 112 then adjusts the detected signal by at least a portion of a calibration unit in order to match the detected signal to the expected signal for the calibrant. It should be understood that the calibration unit is an arbitrary unit of measure specific to a particular calibration, and accordingly, reference to "one," "more than one," "less than one," and/or "a portion of" a "calibrated unit" may reference the same amount of absolute time. Subsequent detected signals (e.g., sample signals of unknown substances) are then adjusted by same amount (e.g., the at least a portion of the calibration unit) in order to accurately compare the detected (sample) signals to the library of substances for identification of constituents of a sample.

In some embodiments, chamber 150 includes from about 10 mg to about 500 g of the calibrant. In some embodiments, chamber 150 includes from about 50 mg to about 250 g of the calibrant, from about 25 mg to about 100 g of the calibrant, or from about 20 mg to about 50 g of the calibrant. More specifically, in some embodiments, chamber 150 includes from about 0.1 g to about 10 g of the calibrant.

In some embodiments, item 152 is a permeation tube (not specifically shown) including the calibrant. The permeation tube is configured to emit the calibrant at a particular, predetermined rate. In some embodiments, the calibrant is emitted from the permeation tube at an emission rate of from about 0.4 µg/min to about 30 µg/min. In some embodiments, the calibrant is emitted from the permeation tube at an emission rate of from about 0.5 µg/min to about 25 µg/min, from about 0.75 µg/min to about 20 µg/min, or from about 0.9 µg/min to about 10 µg/min. In some embodiments, the calibrant is emitted from the permeation tube at an emission rate of from about 1 µg/min to about 2 µg/min. In other embodiments, chamber 150 includes a control valve (not shown) configured to release the calibrant at a particular, predetermined rate. In some embodiments, the control valve releases the calibrant at an emission rate of from about 0.4 µg/min to about 30 µg/min. In some embodiments, the control valve releases the calibrant at an emission rate of from about 0.5 µg/min to about 25 µg/min, from about 0.75 µg/min to about 20 µg/min, or from about 0.9 µg/min to about 10 µg/min. In some embodiments, the control valve releases the calibrant at an emission rate of from about 1 µg/min to about 2 µg/min. The gas flows into chamber 150 and "picks up" the calibrant released from the permeation tube and/or by the control valve for analysis by detector 112 and calibration of the detector 112.

In some embodiments, calibration of detector 112 includes ionization of the calibrant in a calibrant gas. Detector 112 detects and records at least one mobility spectrum of the ionized calibrant. In some embodiments, detector 112 additionally or alternatively detects and records at least one differential mobility spectrum and/or mass spectrum, depending upon the type of detector 112. Accordingly, where "mobility spectrum" is used herein, it should be understood to refer generally to any of these spectra. In the exemplary embodiment, the mobility spectra are plotted on axes corresponding to a drift time and a "count" or "magnitude". Where other types of spectra are detected, one or more of the axes correspond to other characteristics, such as compensation voltage or mass. Drift time is an inherent characteristic of a substance. Therefore, detecting a drift time of a substance enables identification of that substance. Each mobility spectrum includes at least one peak, wherein a particular peak of the mobility spectrum corresponds to the detected calibrant. Detector 112 identifies the drift time associated with the peak, and adjusts the detected drift time of the peak to a known drift time associated with the calibrant.

In some embodiments, detector 112 accesses a library of known or expected signals or mobility spectra, each spectrum associated with a particular substance. These known mobility spectra are developed by performing a base calibration for each substance in the library. The base calibration includes analyzing a known mobility spectrum for each known substance, or, more specifically, analyzing and identifying at least one peak position of the known substance. The known mobility spectra, including the corresponding peak positions, are stored in the library. Detector 112 identifies the known spectrum for the calibrant and adjusts the detected drift time of the detected calibrant peak to match a known drift time associated with a known calibrant peak. For example, in some embodiments, detector 112 shifts the peak up or down a drift time axis by X ms. Detector 112 records this adjustment (e.g., +X ms) as one or more calibration unit(s).

In some embodiments, detector 112 is calibrated at fixed intervals. Moreover, in some embodiments, the fixed intervals are pre-determined, for example, by an operator (not shown) of system 100 and/or by pre-programming system 100. In some embodiments, the fixed interval is between about 10 minutes and about 24 hours, between about 15 minutes and about 8 hours, between about 30 minutes and about 4 hours, between about 1 hour and about 3 hours, about 2 hours, or about 30 minutes. In some embodiments, the fixed interval is flexible in that additional calibrations are performed before the fixed interval has fully elapsed. For example, in some embodiments, system 100 is pre-programmed to initiate calibration in the event of a pressure change outside of a certain threshold. As another example, system 100 is pre-programmed to shorten one or more intervals if a quality of the calibration is low (e.g., low confidence in the calibration results or poor verification). Additionally or alternatively, detector 112 is calibrated "on-demand," at a time determined by a user (e.g., an operator) of system 100. For example, in some embodiments, detector 112 is calibrated on a sample-by-sample basis. In some embodiments, detector 112 is calibrated substantially continuously, for example, before and/or after each sample is analyzed.

In some embodiments, a temperature of chamber 150 is maintained before, during, and/or after calibration of detector 112. More particularly, in certain embodiments, the temperature of chamber 150 is maintained between about 0° C. and about 200° C., between about 10° C. and about 150° C., between about 15° C. and about 100° C., or between about 20° C. and about 50° C. The temperature is maintained within chamber 150 by at least one of heating, cooling, and combinations thereof. For example, in some embodiments, system 100 includes one or more heating elements and/or cooling elements (not shown), such as heaters, fans, heating/cooling blocks, and/or any other heating/cooling elements. Additionally or alternatively, the temperature is maintained passively, for example, at an ambient temperature of an environment around system 100.

As shown in FIGS. 3 and 4A, in embodiments, first valve 154 is a three port valve including a first port 158, a second port 160, and a third port 162. Similarly, second valve 156 is a three port valve including a first port 164, a second port 166, and a third port, 168. During normal operation the flow path of dry air enters port 166 and leaves port 168 of valve 156, thus bypassing ICA 150. As shown in FIG. 3, the ICA bypass line connects to the second port 160 (port 2) of valve 154. In the alternate embodiment of the circuit shown in FIG. 4A, the ICA bypass line connects to the third port 162 (port 3) of valve 154.

During calibration, valves 154 and 156 are switched. The flow path of air enters port 166 and leaves port 164 of valve 156, passes through ICA 150 (in particular calibrant 152), enters port 158 and leaves port 160 of solenoid valve 154.

During normal operation, valve 154 is closed such that port 158 is not in flow communication with port 160. The time interval for calibration is very small in comparison to the overall use of the system 100. Valves 154 and 156 are in the first state or normal operation for more than 95% of operation time of ETD 100. It is during this "normal-use" time that moisture slowly accumulates in ICA 150 as it does not have dry air flow moving through it.

It is well established that, upon following a shift of normal use, ETDs go through a thermal cleaning protocol (also described above as the nightly burn protocol). The temperatures of various subsystems (detector and desorber) are increased and purged of contaminants collected during use. In the present specification, ICA 150 is also purged as part of this thermal cleaning protocol and at regular intervals throughout the day, in accordance with embodiments of the present specification. In embodiments, ICA 150 may be opened to the flow path not to provide calibration to ETD 100, but to reduce the amount of moisture in ICA 150.

Upon completion of the thermal cleaning protocol, the moisture level in ICA 150 is reduced to normal levels to ensure proper calibration. In some ETD systems, a nightly cleaning operation is performed by an embedded software feature, where the ETD system elevates temperatures and opens valves in a way to clean the ETD system so it is ready for the next day's operation. In embodiments, an additional software feature is provided that lowers the humidity levels in the ICA of the ETD system, by opening additional valves in flow communication with at least one of the detector pump, detector, ICA, or desorber as a part of the nightly cleaning operation.

In context of embodiments of the present specification, the relative humidity (RH) of the ICA 150 is measured before entering curtain flow port 116 by placing an RH sensor within the ICA permanently, removably, and/or temporarily. Alternatively, the system operation is optimized in test systems with an RH sensor and then commercially deployed without an RH sensor. Embodiments of the present specification ensure that the relative humidity in the ICA is constant. In embodiments, methods and systems of the present specification ensure that relative humidity within the ICA does not increase by more than 6% during a day in which the corresponding ETD is operational. In embodiments, methods and systems of the present specification ensure that relative humidity within the ICA does not increase by more than 2%. Low humidity levels ensure that peak shifts will be minimized to accurately measure and identify samples based upon drift times. In some embodiments, the methods of the present specification are implemented regularly, such as for example, every 30 minutes, to ensure accuracy of operation of the ICA.

Figure 4B:
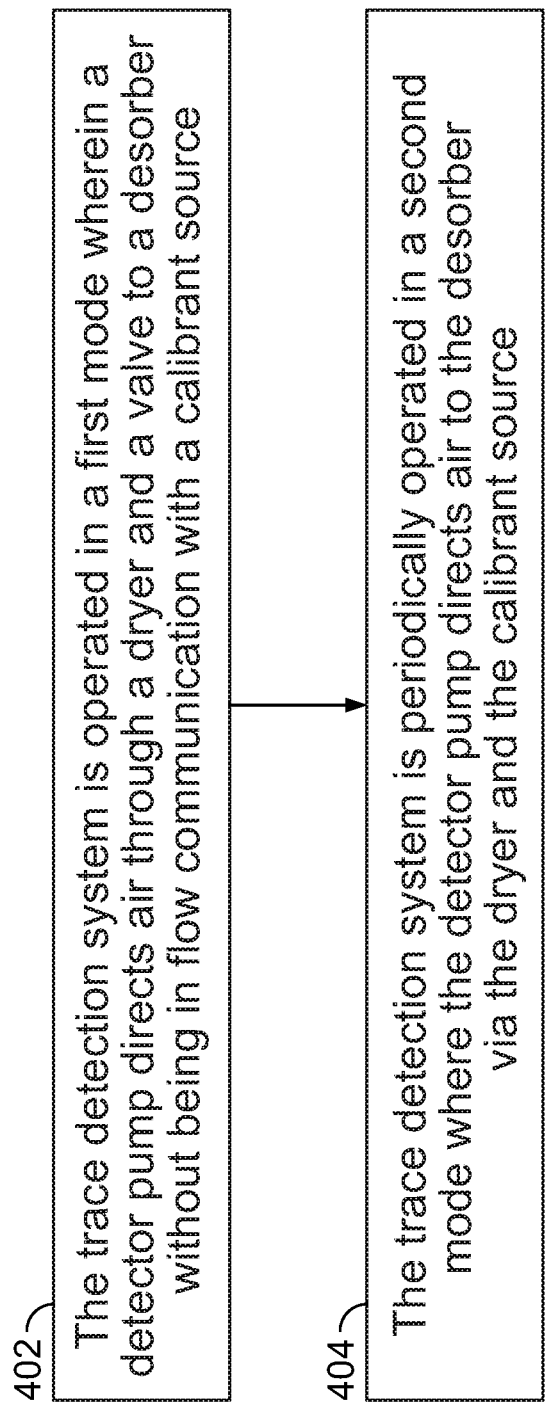
FIG. 4B is a flowchart illustrating a method for reducing humidity within an internal calibration chamber of a trace detection system, in accordance with an embodiment of the present specification.

FIG. 4B is a flowchart illustrating a method for reducing humidity within an internal calibration chamber of a trace detection system, in accordance with an embodiment of the present specification. As described above with reference to FIGS. 2, 3 and 4A, the trace detection system, in which the method shown in FIG. 4B is implemented, comprises a detector pump 102 coupled with a dryer 108, a desorber 122 in flow communication with the detector pump 102, a detector 112 in flow communication with the desorber 122, and an internal calibration assembly 150 defined by a housing and having a first valve 154, a second valve 156, and calibrant source 152 positioned within the housing. At step 402, the trace detection system is operated in a first mode wherein a detector pump directs air through a dryer, and a valve to a desorber without being in flow communication with a calibrant source. In an embodiment, referring to FIGS. 2, 3, 4A and 4B, at step 402, the trace detection system is operated in a first mode wherein the detector pump 102 directs air through the dryer 108, the second valve 156 and to the desorber 122 without being in flow communication with the calibrant source 152. At step 404, the trace detection system is periodically operated in a second mode wherein the detector pump directs air to the desorber via the dryer, and the calibrant source. In an embodiment, referring to FIGS. 2, 3, 4A and 4B, at step 404, the trace detection system is periodically operated in a second mode wherein the detector pump 102 directs air to the desorber 122 via the dryer 108, the first valve 154, the calibrant source 152, and the second valve 156. In various embodiments, step 404 is performed at regular intervals in a day of operating the trace detection system, wherein the interval varies from at least 30 minutes to at most 24 hours. In an embodiment, step 404 is performed at least once during a nightly cleaning process of the trace detection system.

Figure 4C:
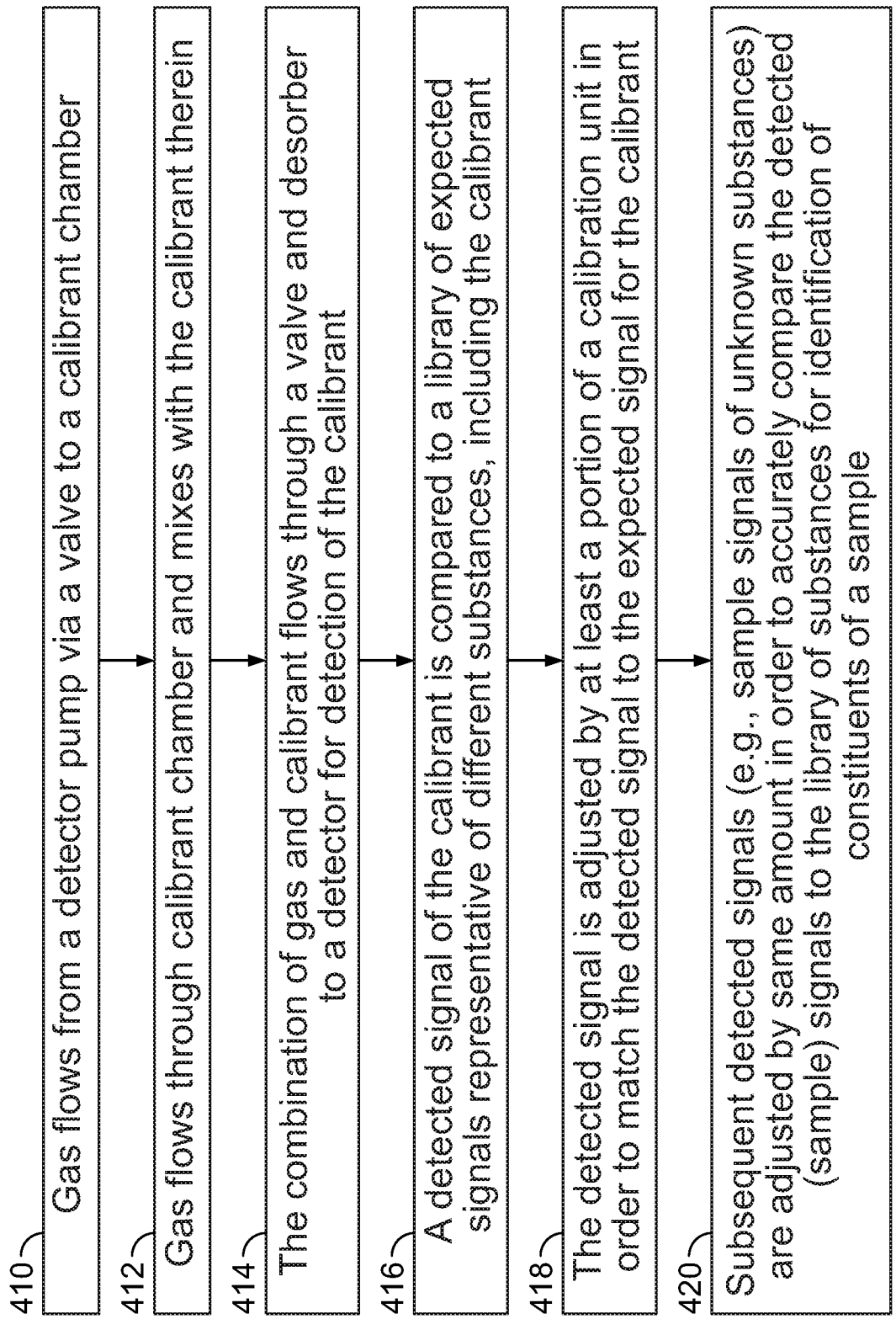
FIG. 4C is a flowchart illustrating a method of calibrating a detector of a trace detection system, in accordance with an embodiment of the present specification.

FIG. 4C is a flowchart illustrating a method of calibrating a detector of a trace detection system, in accordance with an embodiment of the present specification. At step 410 gas flows from a detector pump via a valve to a calibrant chamber. In an embodiment, the gas includes at least one of ambient air, purified air, dried air, purified nitrogen, and combinations thereof. At step 412, the gas flows through calibrant chamber and mixes with the calibrant therein. At step 414 the combination of gas and calibrant flows through a valve and desorber to a detector for detection of the calibrant. At step 416 a detected signal of the calibrant is compared to a library of expected signals representative of different substances, including the calibrant. At step 418, the detected signal is adjusted by at least a portion of a calibration unit in order to match the detected signal to the expected signal for the calibrant. In various embodiments, the calibration unit is an arbitrary unit of measure specific to a particular calibration, and accordingly, reference to "one," "more than one," "less than one," and/or "a portion of" a "calibrated unit" may reference the same amount of absolute time. At step 420, subsequent detected signals (e.g., sample signals of unknown substances) are adjusted by same amount in order to accurately compare the detected (sample) signals to the library of substances for identification of constituents of a sample.

Figure 5:
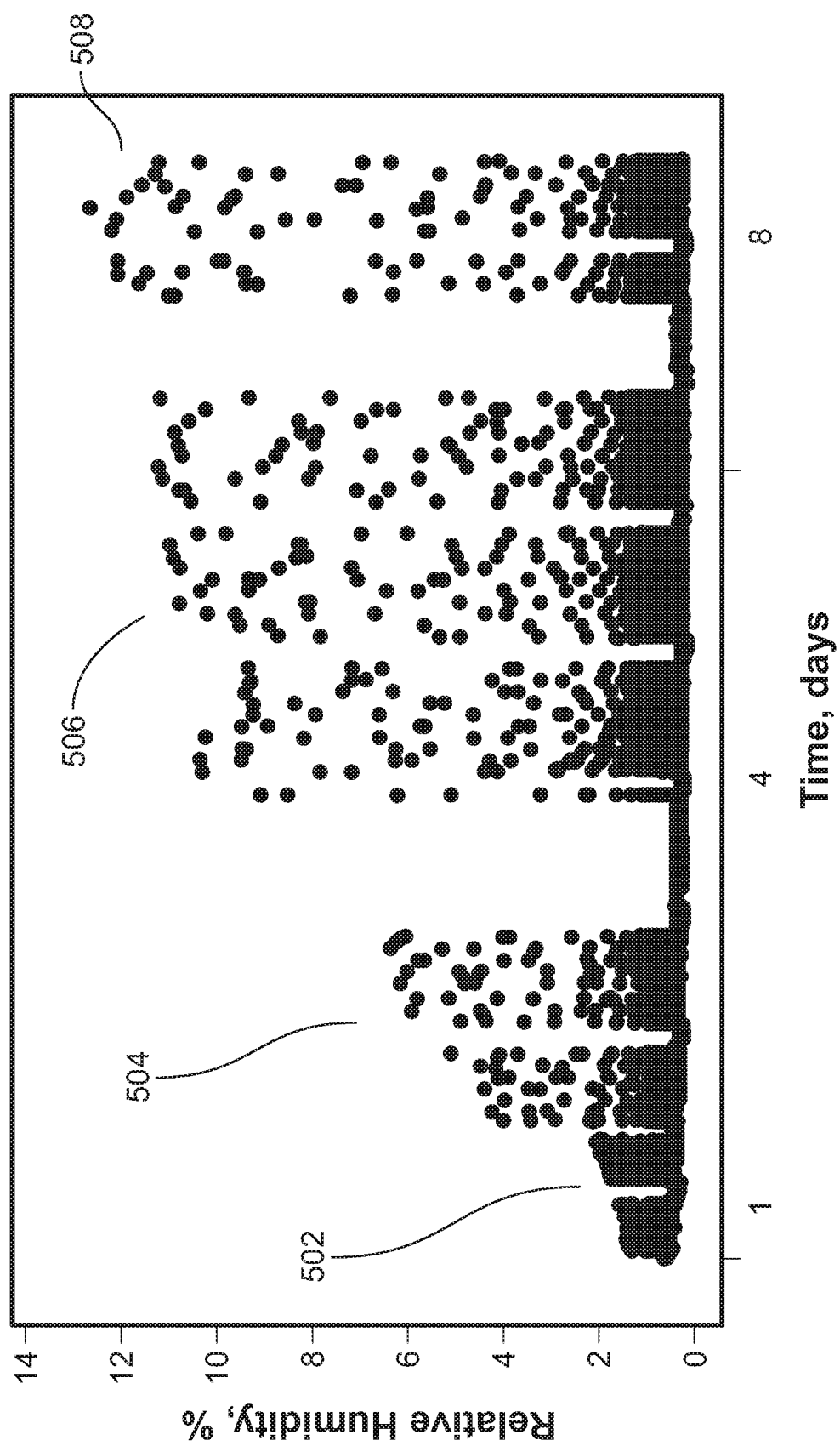
FIG. 5 is a graph illustrating an exemplary scenario where RH (y-axis) in the ICA is monitored over several days (x-axis) when the ICA was not purged of humidity.

FIG. 5 is a graph illustrating an exemplary scenario where RH (y-axis) in the ICA is monitored over a few days (x-axis) when the ICA was not purged of humidity during these days. In the exemplary scenario, the ICA was purged with dry air for about 40 minutes on the first day 502, before initiating operation of the corresponding ETD. The graph illustrates that while the first few days 504 are near a target RH level, which refers a desirable RH level within the ICA, once ETD is operating over several days 506, 508, the RH levels gradually start building up. FIG. 5 thus indicates that there is a need to maintain humidity within the ICA.

Figure 6:
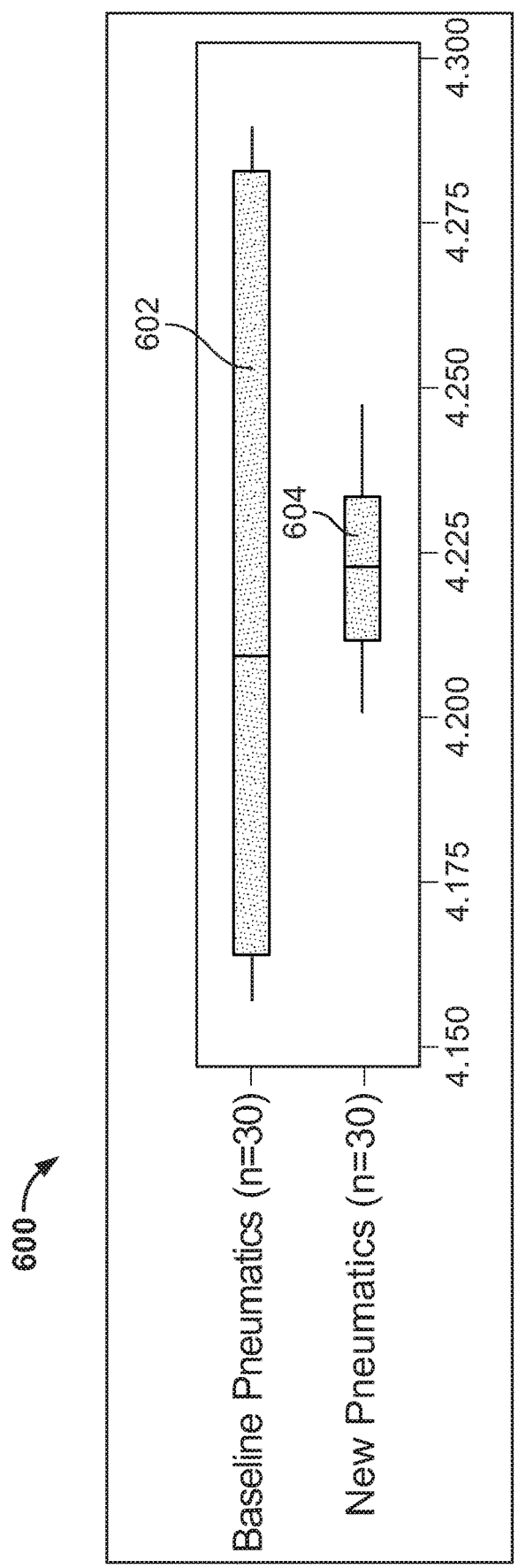
FIG. 6 is another exemplary graph illustrating a comparison of distribution of calibrations with and without using embodiments of the present specification.

FIG. 6 is another exemplary graph illustrating a comparison of distribution of calibrations with and without using embodiments of the present specification. Referring to graph 600, a bar 602 illustrates the distribution of calibrations without using embodiments of the present specification, where the RH was approximately 12%. A bar 604 illustrates the distribution using embodiments of the present specification, when the reduced RH ranged from 4 to 7.5%. There is a reduction of 75% in the standard deviation, observed from the graph. The graph indicates that embodiments of the present specification improve reproducibility of the calibrations in ETDs.

Figure 7A:
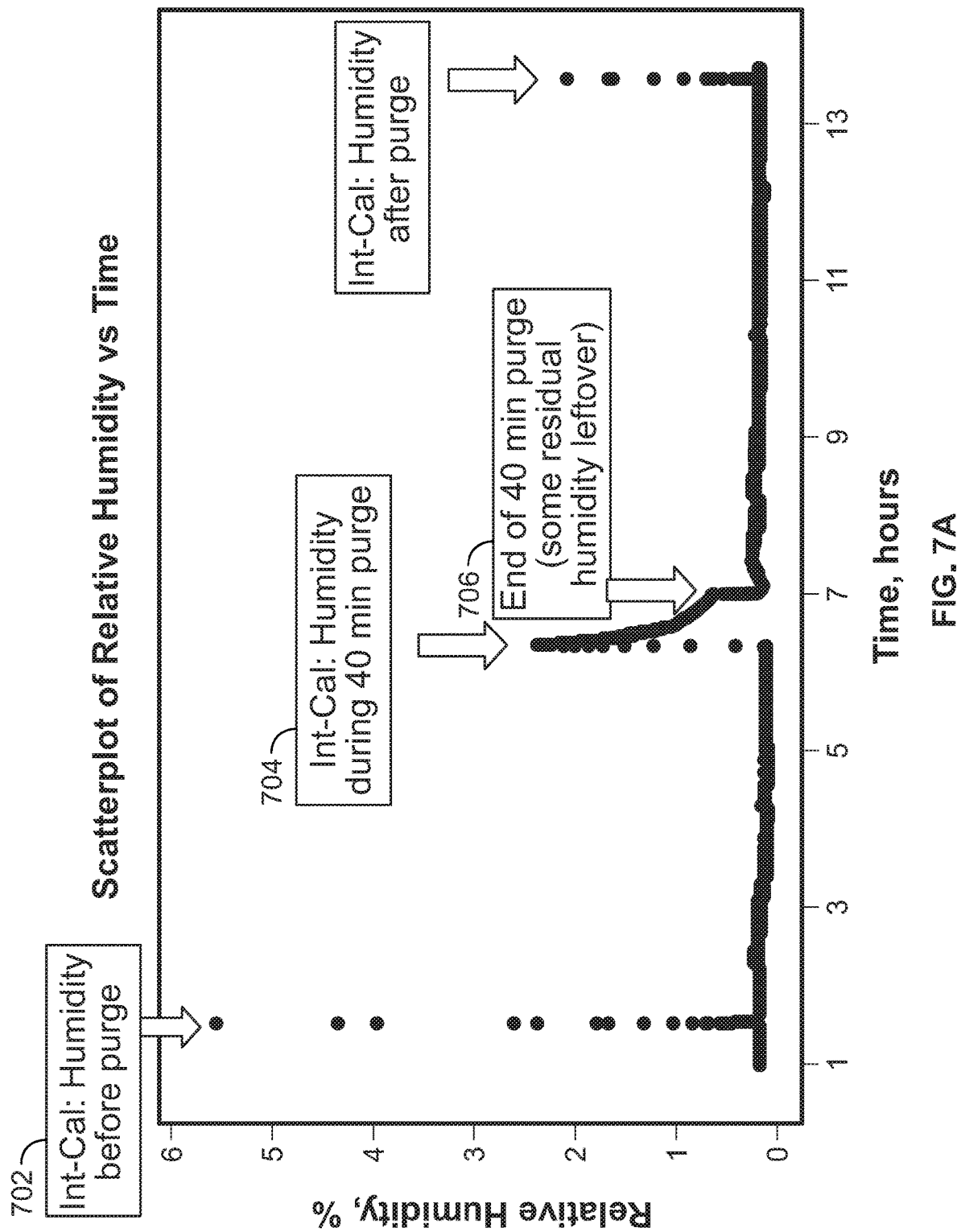
FIG. 7A is an exemplary graph illustrating the RH levels (y-axis) for an active ETD over a day.
Figure 7B:
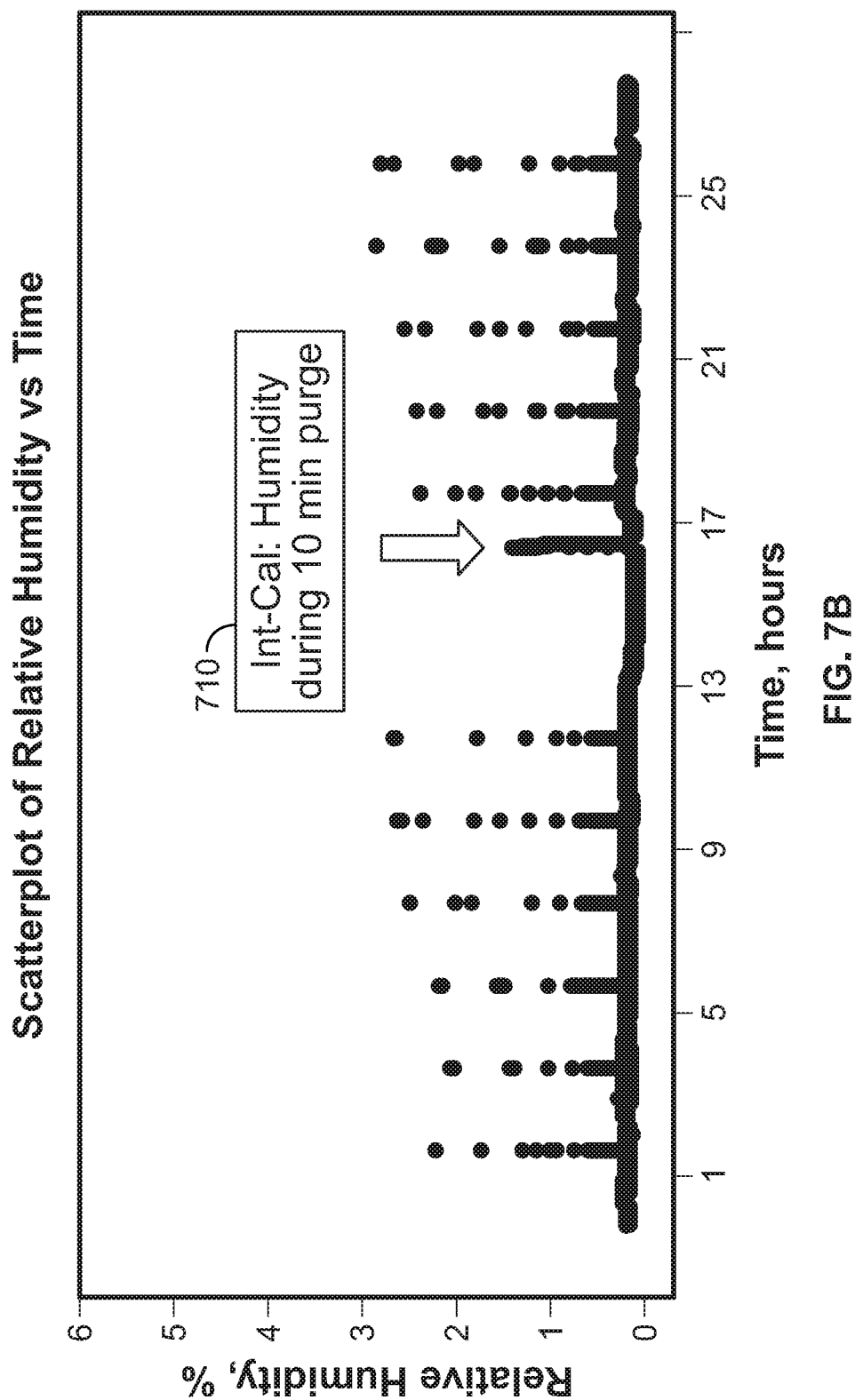
FIG. 7B is another exemplary graph illustrating an effect of daily 10 minute purging subsequent to the 40 minute purging of the ETD shown in FIG. 11A.

In some embodiments, duration of the purge of dry air of the ICA may vary in order to reach a target RH level. The variation in the duration of purge may be based on one or more factors, such as the time since the ICA was at the target RH level, the duration of operation of the ETD, the environment, or any other factors that may influence a duration and/or frequency of purging in accordance with embodiments of the present specification. FIG. 7A is an exemplary graph illustrating the RH levels (y-axis) for an active ETD over a day. In the exemplary representation, at 702 the humidity level before purge are high. A 40 minute purge is performed in the window between 704 and 706, when the humidity level continuously decreases. FIG. 7B is another exemplary graph illustrating an effect of daily 10 minute purging subsequent to the 40 minute purging of ETD shown in FIG. 7A. The graph shows that daily (or nightly) 10 minute purges, such as the one shown at 710, slows humidity accumulation. Therefore, it may be derived that once an ICA has reached its target humidity level such as by using the embodiments of the present specification, a daily 10 minute purge of the ICA keeps the ICA within 18% of the RH over the subsequent two days. Though this slows the humidity accumulation, it does not completely stop it.

Figure 7C:
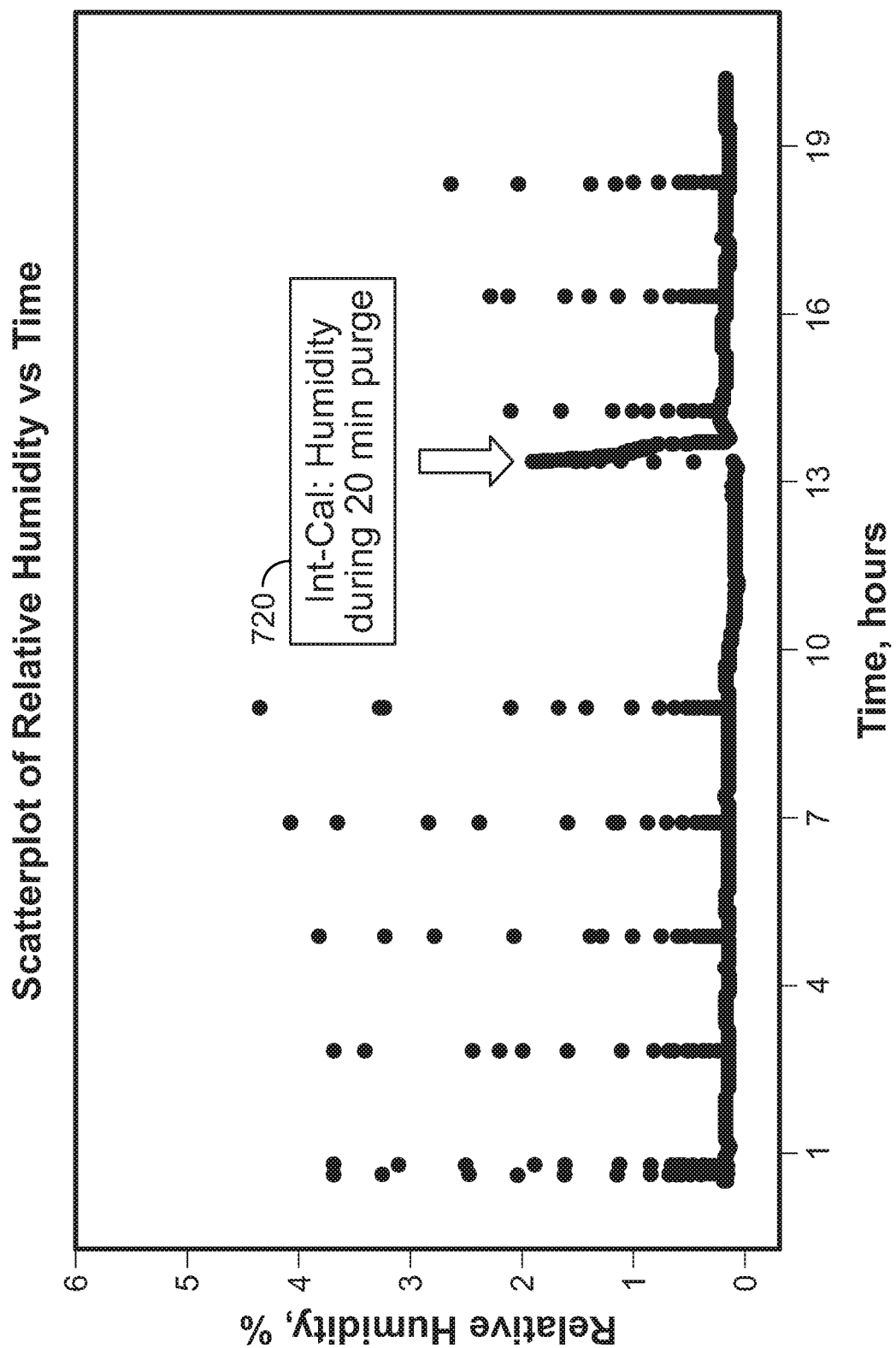
FIG. 7C is another exemplary graph illustrating the effect on RH with a 20 minute daily purge of ICA in an active ETD using embodiments in accordance with the present specification.

FIG. 7C is another exemplary graph illustrating the effect on RH with a 20 minute daily purge of ICA in an active ETD using embodiments in accordance with the present specification. In the exemplary scenario, a 20 minute purge, such as the one shown at 720, brings the ICA back to target humidity, therefore suggesting that purging for 20 minutes may be better than for 10 minutes, to maintain an active ETD.

Persons skilled in the art may appreciate that the duration and frequency of purging the ICA with dry air may be varied to match the requirement of an active ETD in order to maintain the humidity levels in the ICA within the target RH.

Figure 8B:
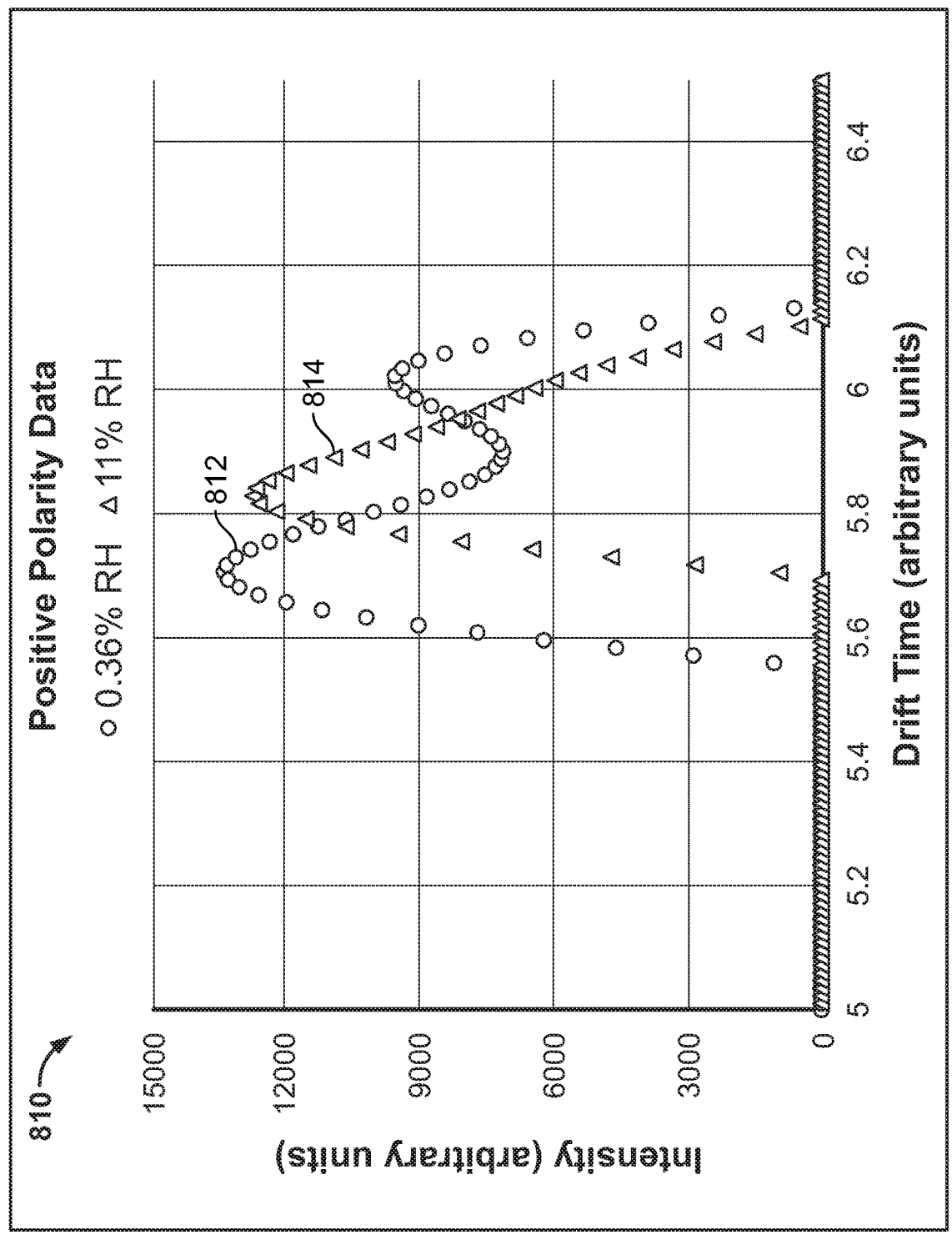
FIG. 8B is a graph illustrating two peaks formed by a dopant material at low humidity levels in an ETD.
Figure 8C:
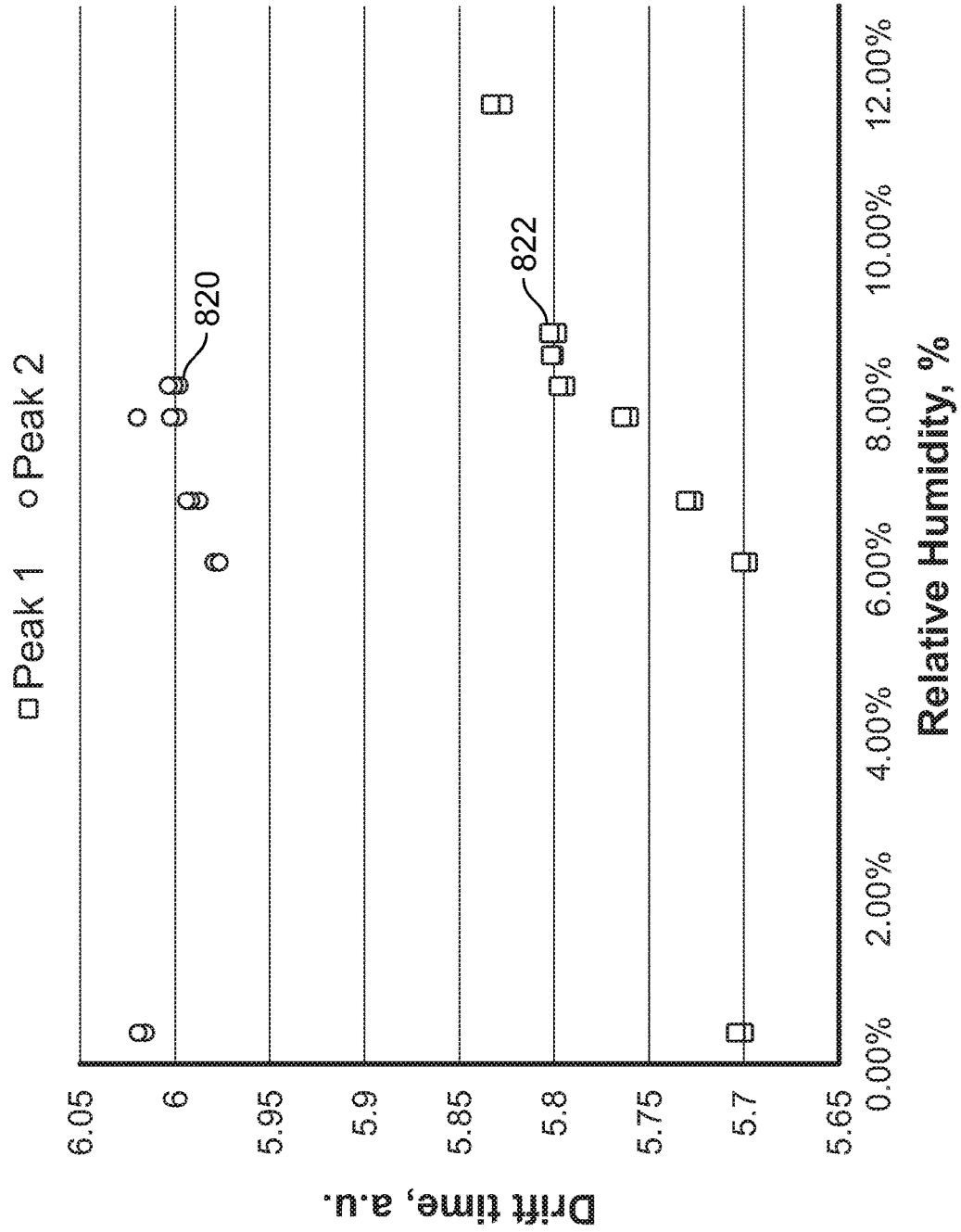
FIG. 8C illustrates a plot of drift time versus relative humidity in an ETD.
Figure 8D:
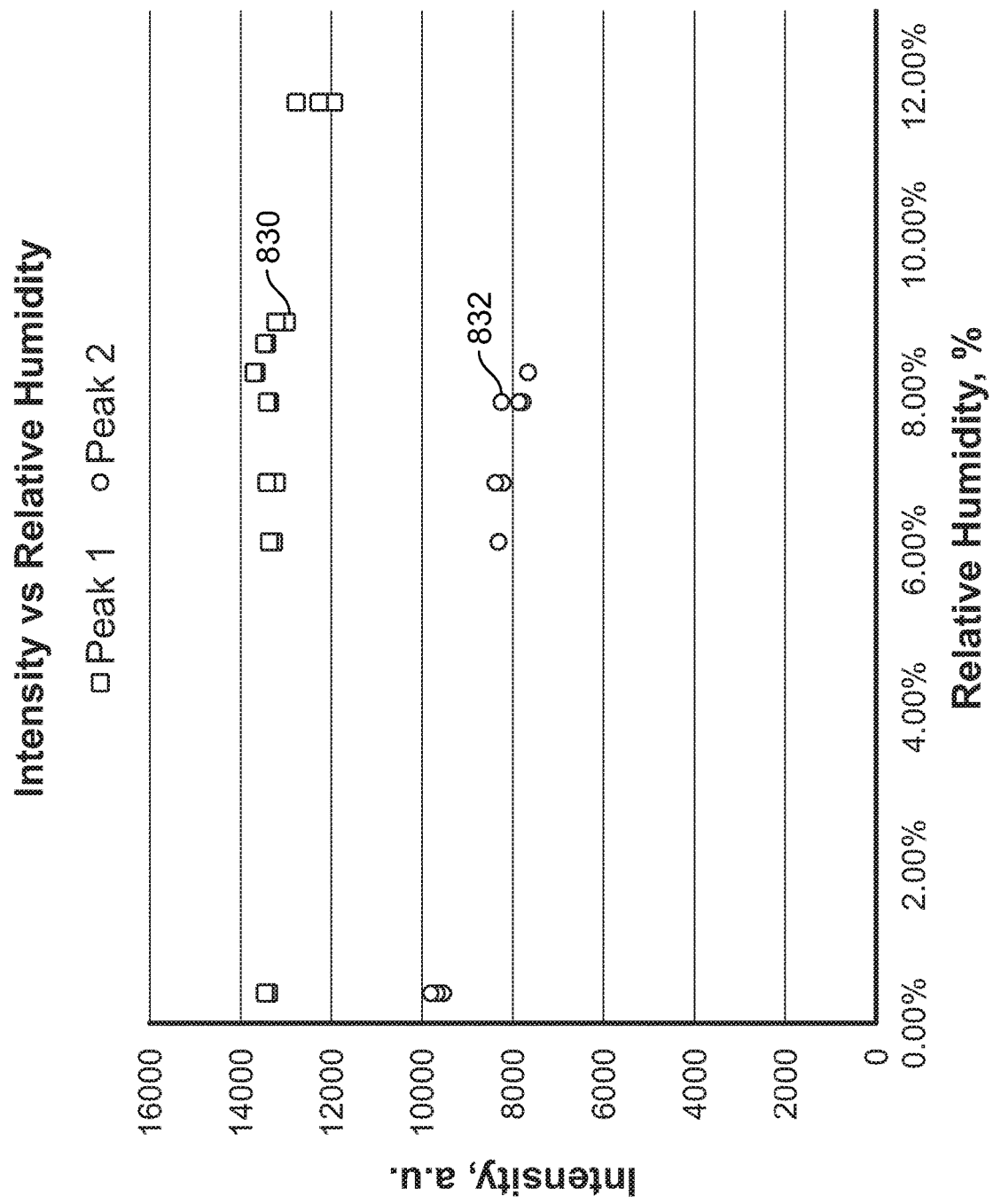
FIG. 8D illustrates a plot of intensity versus relative humidity in an ETD.

In various embodiments, during analysis, high humidity levels within an active ETD are identified by the absence of two peaks of a dopant material. FIG. 8A illustrates a table showing the peaks formed by a dopant in a positive polarity region at different humidity levels. As shown in table 802, at low humidity levels there are two peaks in the positive long region, wherein peak 1 is around 5.7 a.u. drift time and peak 2 is around 6.0 a.u. drift time. Peak 2 disappears at approximately 8% humidity (RH). FIG. 8B is a graph illustrating the two peaks formed by a dopant material at low humidity levels in an ETD. Graph 810 illustrates plot 812 formed in the positive polarity region at approximately 0.36% humidity and plot 814 formed at 11% humidity. FIG. 8C illustrates a plot of drift time versus relative humidity in an ETD. As shown peak one 820 drifts to the right at higher humidity levels. Peak two 822 shows little to no drift and merges with peak one around 8.0% humidity (RH). Both peaks 820, 822 are present at 7.75% humidity (RH). An ETD system is determined as having a high humidity when peak two 822 disappears. FIG. 8D illustrates a plot of intensity versus relative humidity in an ETD. As shown, the intensity of peak 1, (830) is between 12,000 and 14,000 and does not change with humidity. The intensity of peak 2, (832) is between 7,000 and 10,000 and decreases with increasing levels of humidity.

Figure 9:
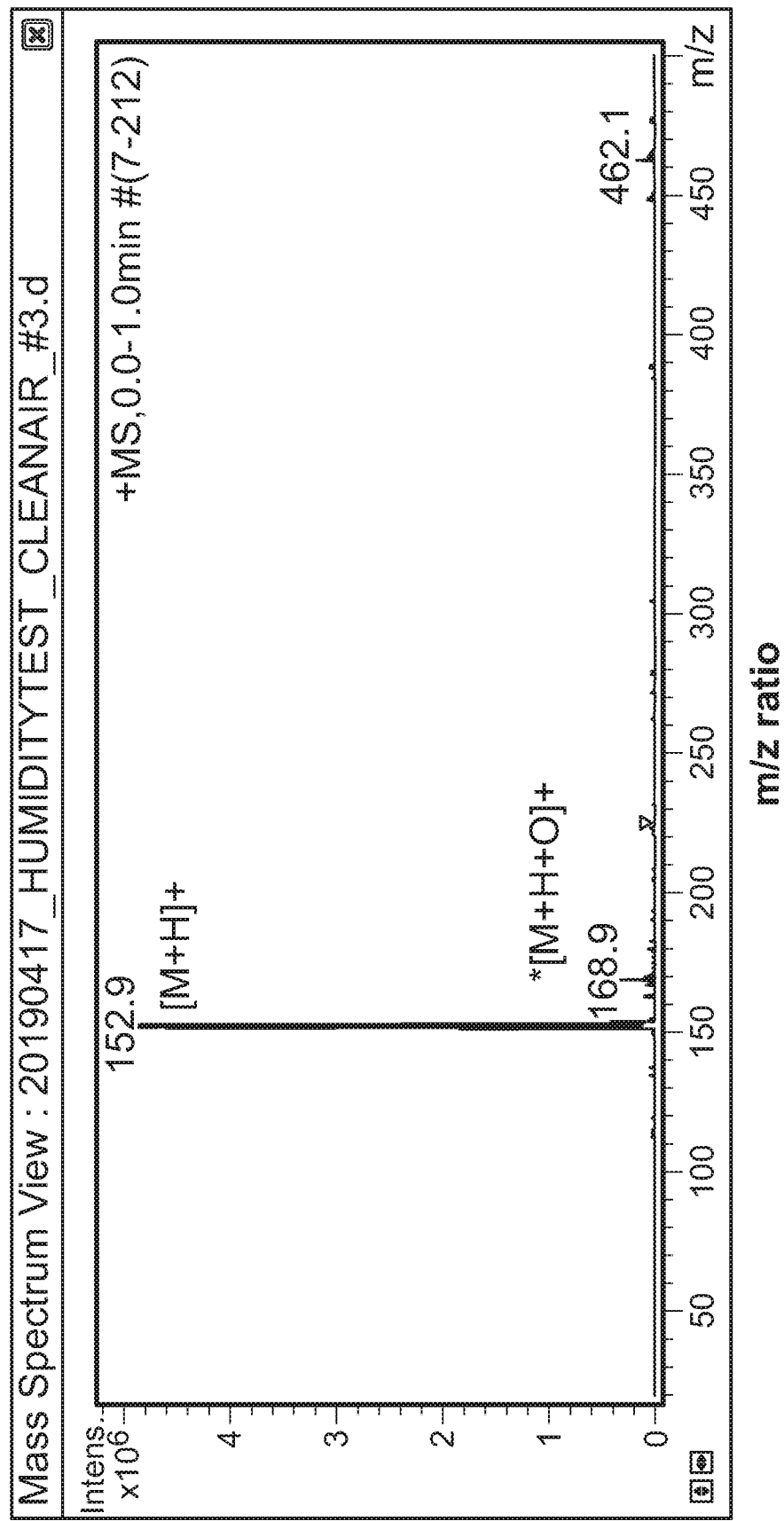
FIG. 9 is a graph illustrating the results of internal calibrant in the ETD of the present specification by using Bruker spectrograph in a positive mode, in the presence of 1.15% humidity in the ETD.

The results of the ETD of the present specification, in an embodiment, were analyzed by using mass spectrometry in order to determine the identity (mass to charge ratio) of the two ion mobility peaks in positive long mode of operation. FIG. 9 is a graph 930 illustrating the results of internal calibrant in the ETD of the present specification by using Bruker spectrometer in a positive mode, in the presence of 1.15% humidity in the ETD.

With reference to graph 930, it is observed that for internal calibrants methylsalycylate and cluster of methylsalycylate with oxygen with ratio of 10:1, ion mobility peaks at 5.7 and 6.0 a.u. in a positive long scan. Starting at 6% to 8% of RH a second peak in positive long is reduced or completely quenched. The presence of a methylsalycylate cluster with oxygen can be used to monitor RH in the internal calibrant block and can be used to determine whether and to what extent the system is clean.

Although specific features of various embodiments of the disclosure may be shown in some drawings and not in others, this is for convenience only. In accordance with the principles of the disclosure, any feature of a drawing may be referenced and/or claimed in combination with any feature of any other drawing. The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for reducing humidity within an internal calibration chamber of a trace detection system, wherein the trace detection system comprises a first pump coupled with a dryer, a desorber in flow communication with the first pump, a detector in flow communication with the desorber, and an internal calibration assembly defined by a housing and having a first valve, a second valve, and a calibrant source positioned within the housing, wherein when the first valve is in a first state it directs flow directly to at least one of the desorber or the second valve and bypasses the calibrant source and wherein, when the first valve is in a second state, it directs flow through the calibrant source and then to the second valve, the method comprising:
   in a first mode of operation,
      operating the first pump to direct air through the dryer in order to form dry air; and
      operating the first valve to place the first valve in the first state, wherein the first valve is configured to receive the dry air and direct the dry air to the desorber without being in flow communication with the calibrant source; and
   in a second mode of operation,
      operating the first pump to direct air through the dryer in order to form dry air; and
      operating the first valve to place the first valve in the second state, wherein the first valve is configured to receive the dry air and direct the dry air through the second valve and the calibrant source to the desorber.

2. The method of claim 1 further comprising, in the first mode of operation, operating the first valve to direct dry air to the desorber without being in flow communication with the second valve.

3. The method of claim 1 wherein, in the second mode of operation, the dry air has a relative humidity of less than 1%.

4. The method of claim 1 wherein the calibrant source comprises a canister of calibration chemical.

5. The method of claim 4 wherein the calibrant is at least one of dibenzylamine, diethylphenylmalonate, diisopropylphenol, 2,4-dimethylpyridine, dioctylphthalate, dinitrotoluene, dipropylene glycol monomethylether, 2,6-di-t-butylpyridine, ethyl salicylate, hexachloroethane, hexaphenylbenzene, 4-methyl-2,6-di-tert-butyl phenol, methyl salicylate, nicotinamide, 4-nitrobenzonitrile, 5-nitrovanillin, pentachloroethane, trihexylamine, or combinations thereof.

6. The method of claim 1 wherein the internal calibrant assembly is not in flow communication with the trace detection system except through the second valve.

7. The method of claim 1 wherein each of the first valve and second valve comprise at least two ports.

8. The method of claim 1 wherein a flow rate of the air in each of the first mode of operation and second mode of operation is in a range from about 5 mL per minute to about 5000 mL per minute.

9. The method of claim 1 wherein, in a given 24 hour period, the second mode of operation is activated at a plurality of intervals wherein each of the plurality of intervals ranges from a minimum of 30 minutes to a maximum of 24 hours.

10. The method of claim 1 wherein the second mode of operation is performed at least once between 10 p.m. and 6 a.m.

11. The method of claim 1 wherein a relative humidity within the internal calibration assembly does not exceed 3%.

12. The method of claim 1 wherein a relative humidity within the internal calibration assembly does not exceed 6%.

13. A trace detection system comprising:
a first housing;
an internal calibration assembly defined by a second housing and having a first valve, a second valve, and calibrant source positioned within the second housing;
a first pump positioned in the first housing and outside the second housing;
a desorber in flow communication with the first pump and positioned in the first housing and outside the second housing;
a detector in flow communication with the desorber and positioned in the first housing and outside the second housing; and
a controller configured to operate the trace detection system in a first mode and in a second mode, wherein, in the first mode of operation, the controller is configured to operate the first pump to direct air through the dryer to form dry air and direct the dry air to the desorber through the first valve without being in flow communication with the calibrant source; and wherein, in the second mode of operation, the controller is configured to operate the first pump to direct air through the dryer to form dry air, and direct the dry air through the second valve and the calibrant source to the desorber.

14. The trace detection system of claim 13 wherein, in the first mode of operation, the controller is configured to operate the first valve to direct the dry air directly to the desorber without being in flow communication with the second valve.

15. The trace detection system of claim 13 wherein, in the second mode of operation, the dry air has a relative humidity of less than 1%.

16. The trace detection system of claim 13 wherein the calibrant source comprises a canister of calibration chemical.

17. The trace detection system of claim 13 wherein the internal calibrant assembly is only in flow communication with other components of the trace detection system through the second valve.

18. The trace detection system of claim 13 wherein each of the first valve and the second valve comprise at least two ports.

19. The trace detection system of claim 13 wherein a flow rate of the dry air in each of the first mode of operation and the second mode of operation is in a range from about 5 mL per minute to about 5000 mL per minute.

20. The trace detection system of claim 13 wherein the calibrant is at least one of dibenzylamine, diethylphenylmalonate, diisopropylphenol, 2,4-dimethylpyridine, dioctylphthalate, dinitrotoluene, dipropylene glycol monomethylether, 2,6-di-t-butylpyridine, ethyl salicylate, hexachloroethane, hexaphenylbenzene, 4-methyl-2,6-di-tert-butyl phenol, methyl salicylate, nicotinamide, 4-nitrobenzonitrile, 5-nitrovanillin, pentachloroethane, trihexylamine, or combinations thereof.

21. The trace detection system of claim 13 wherein the controller is configured to operate the second mode of operation at regular intervals in a 24 hour period, wherein a time period of the regular intervals varies from a minimum of 30 minutes to a maximum of 24 hours.

22. The trace detection system of claim 13 wherein the controller is configured to operate the second mode of operation at least once during a nighttime cleaning process of the trace detection system.

23. The trace detection system of claim 13 wherein a relative humidity within the internal calibration assembly does not exceed 3%.

24. The trace detection system of claim 13 wherein a relative humidity within the internal calibration assembly does not exceed 6%.

* * * * *